United States Patent [19]

Baker et al.

[11] Patent Number: 5,693,083
[45] Date of Patent: Dec. 2, 1997

[54] THORACIC GRAFT AND DELIVERY CATHETER

[75] Inventors: Steve G. Baker, Sunnyvale; Michael D. Dake, Stanford; David C. Dillow, Cupertino; Arnold Escano, San Jose, all of Calif.

[73] Assignee: EndoVascular Technologies, Inc., Menlo Park, Calif.

[21] Appl. No.: 358,067

[22] Filed: Dec. 15, 1994

Related U.S. Application Data

[63] Continuation-in-part of Ser. No. 102,576, Aug. 5, 1993, abandoned, which is a continuation-in-part of Ser. No. 553,530, Jul. 13, 1990, Pat. No. 5,275,622, which is a continuation-in-part of Ser. No. 166,093, Mar. 9, 1988, Pat. No. 5,104,399, which is a continuation-in-part of Ser. No. 940,907, Dec. 10, 1986, Pat. No. 4,787,899, which is a continuation of Ser. No. 559,935, Dec. 9, 1993, abandoned.

[51] Int. Cl.⁶ .................................................. A61F 2/06
[52] U.S. Cl. .................................................. 623/1; 606/195
[58] Field of Search .................... 623/1, 12; 606/195; 600/36

[56] References Cited

U.S. PATENT DOCUMENTS

| | | |
|---|---|---|
| 3,805,301 | 4/1974 | Liebig . |
| 4,047,050 | 9/1977 | Arpesani . |
| 4,140,126 | 2/1979 | Choudhury ........................ 623/1 |
| 4,190,909 | 3/1980 | Ablaza . |
| 4,617,932 | 10/1986 | Kornberg ........................ 600/36 |
| 4,681,110 | 7/1987 | Wiktor . |
| 4,830,003 | 5/1989 | Wolff et al. . |
| 4,872,874 | 10/1989 | Taheri . |
| 4,913,141 | 4/1990 | Hillstead ........................ 606/108 |
| 4,950,227 | 8/1990 | Savin et al. . |
| 4,954,126 | 9/1990 | Wallsten . |
| 4,957,669 | 9/1990 | Primm . |
| 5,071,407 | 12/1991 | Termin et al. . |
| 5,078,720 | 1/1992 | Burton et al. . |
| 5,123,919 | 6/1992 | Sauter et al. . |
| 5,151,105 | 9/1992 | Kwan-Gett . |
| 5,207,695 | 5/1993 | Trout, III . |
| 5,282,824 | 2/1994 | Gianturco . |
| 5,282,847 | 2/1994 | Trescony et al. . |
| 5,314,468 | 5/1994 | Ramos Martinez . |
| 5,316,023 | 5/1994 | Palmaz et al. . |
| 5,387,235 | 2/1995 | Chuter ........................ 623/1 |
| 5,405,378 | 4/1995 | Strecker ........................ 623/12 |
| 5,464,449 | 11/1995 | Ryan ........................ 623/1 |

FOREIGN PATENT DOCUMENTS

| | | | |
|---|---|---|---|
| 0656 198 A2 | 2/1991 | European Pat. Off. | .......... A61F 2/06 |
| 0505 686 A1 | 9/1992 | European Pat. Off. | .......... A61F 2/06 |
| 621016 | 10/1994 | European Pat. Off. | .......... 623/1 |
| 2245495 | 1/1992 | United Kingdom | .......... 623/1 |
| WO 95/01761 | 7/1994 | WIPO . | |

*Primary Examiner*—Michael J. Milano
*Attorney, Agent, or Firm*—Fulwider Patton Lee & Utecht, LLP

[57] ABSTRACT

A delivery catheter having an inner catheter assembly, an inferior capsule catheter, and a capsule jacket assembly for use in deploying a graft having a compressible and expandable attachment systems in the thoracic region of an aorta. The graft is comprised of a tubular member having superior and inferior ends, each having an attachment system with wall engaging members secured thereto and is crimped along its midsection to resist kinking and elongation. The delivery catheter includes an inferior capsule assembly for releasably retaining the inferior attachment system of the graft and a superior capsule assembly for releasably retaining the superior attachment system of the graft as well as a releasing system for maintaining the attachment systems in a compressed configuration and for facilitating expansion of the attachment systems. The delivery catheter also includes an anti-elongation wire attached to the inner catheter assembly to prevent stretching of the delivery catheter during deployment of the graft within the aorta. Upon removing the attachment systems from the capsule, the releasing system functions to allow the attachment systems to assume their expanded configuration and engage the walls of the aorta. The graft and attachment systems remain in the vessel after the delivery catheter is withdrawn.

44 Claims, 9 Drawing Sheets

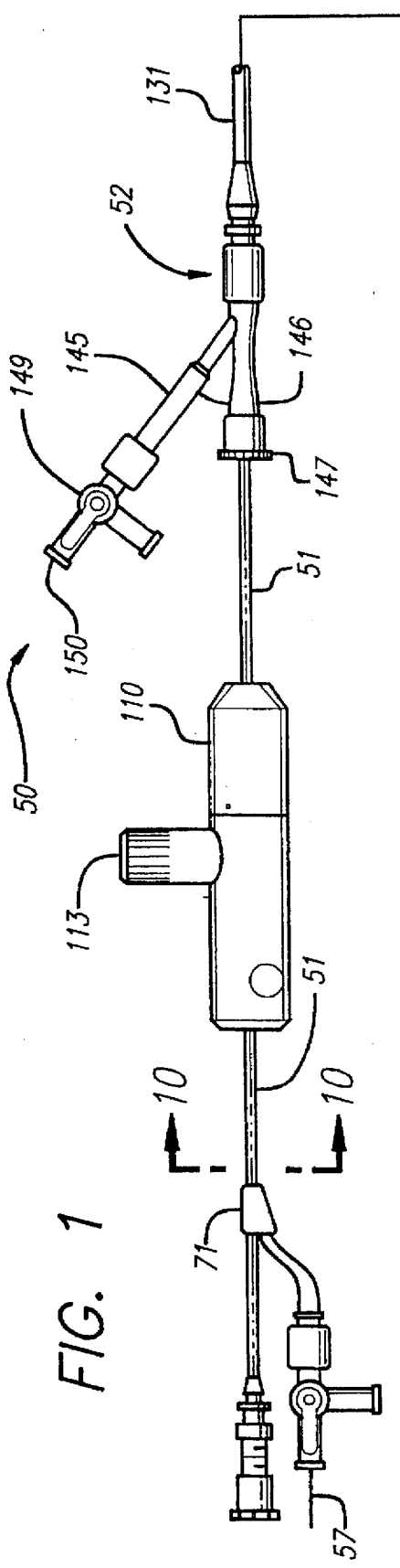
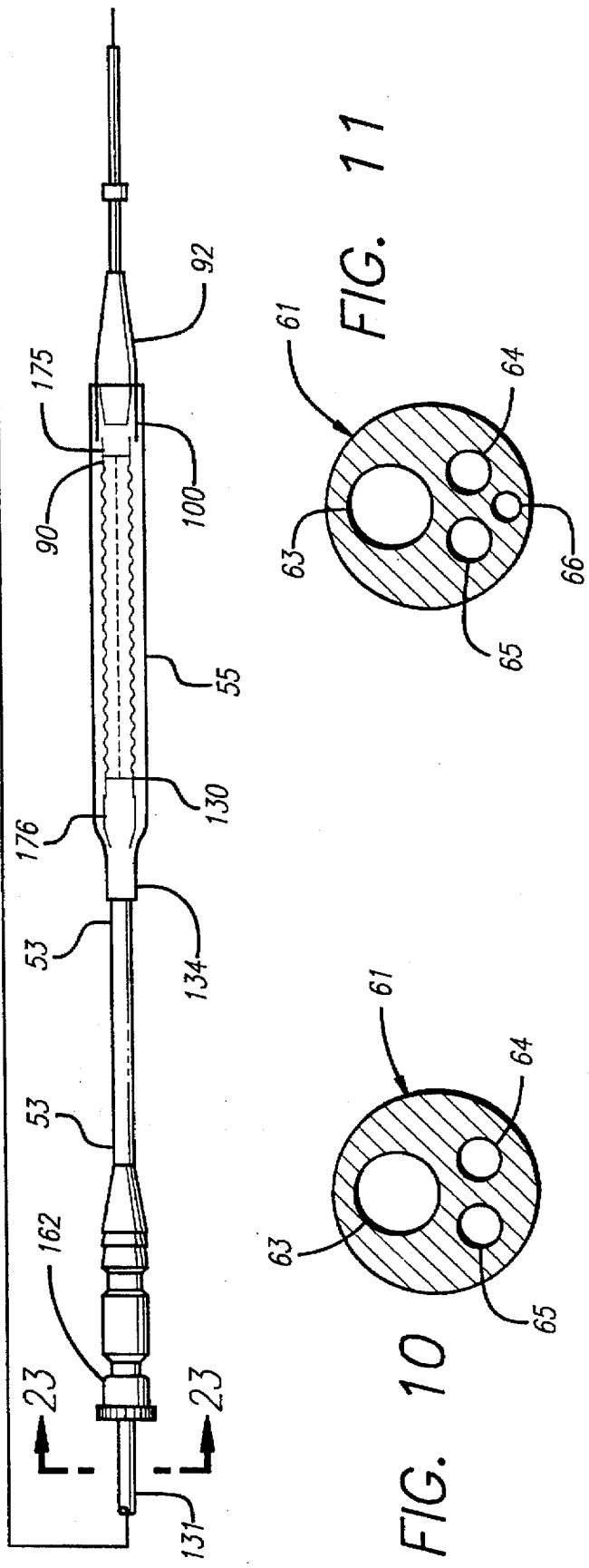

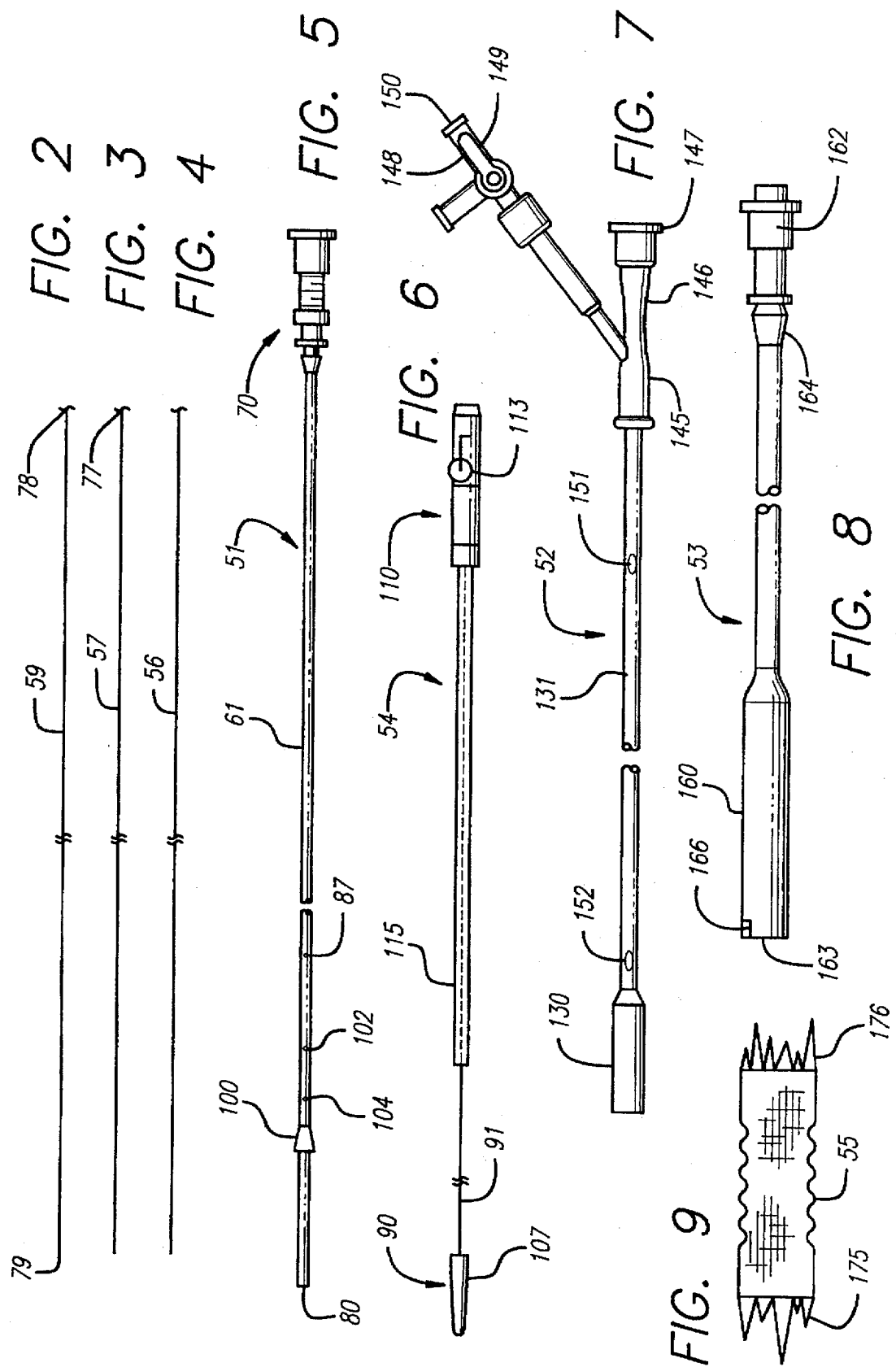

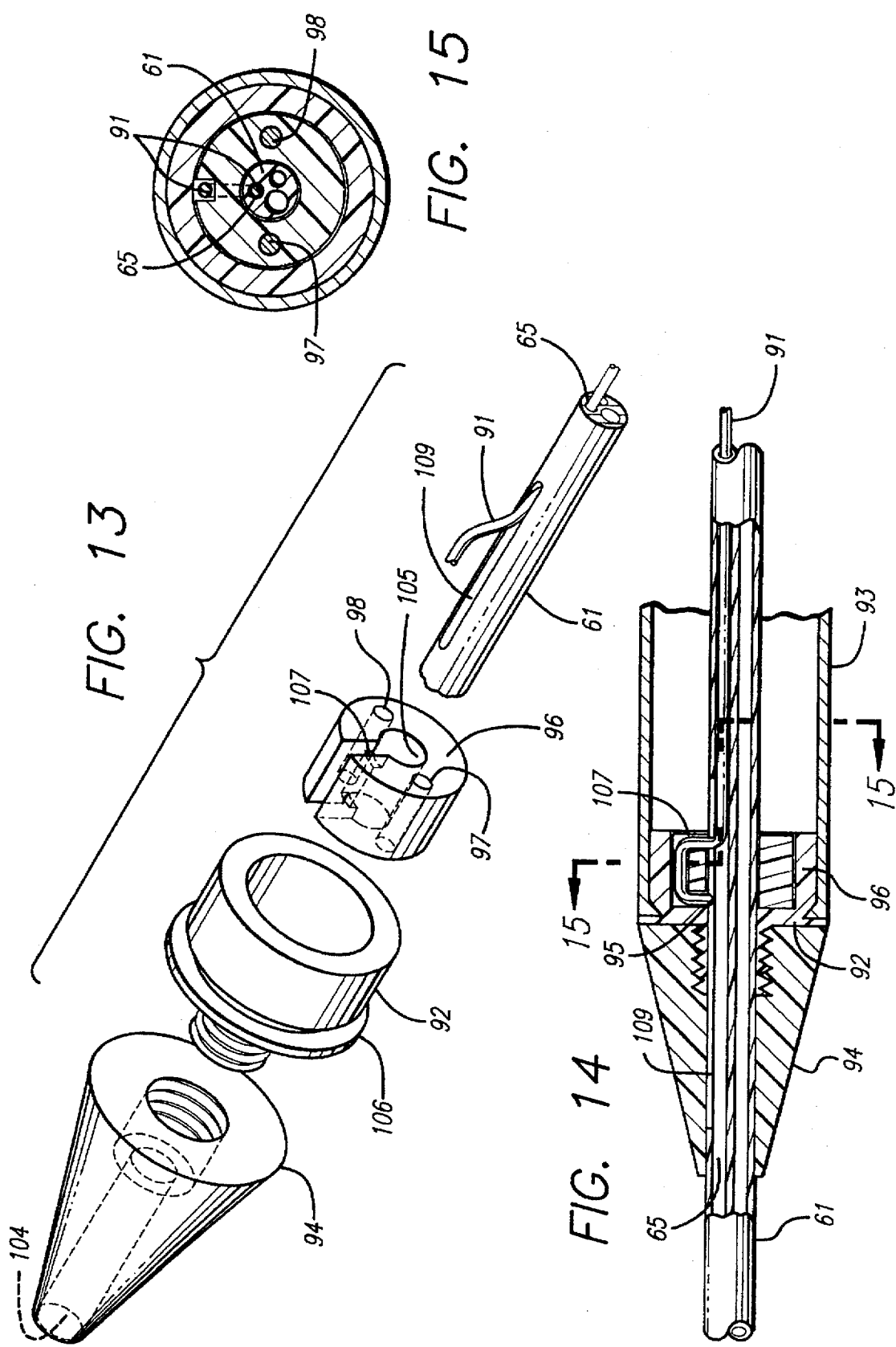

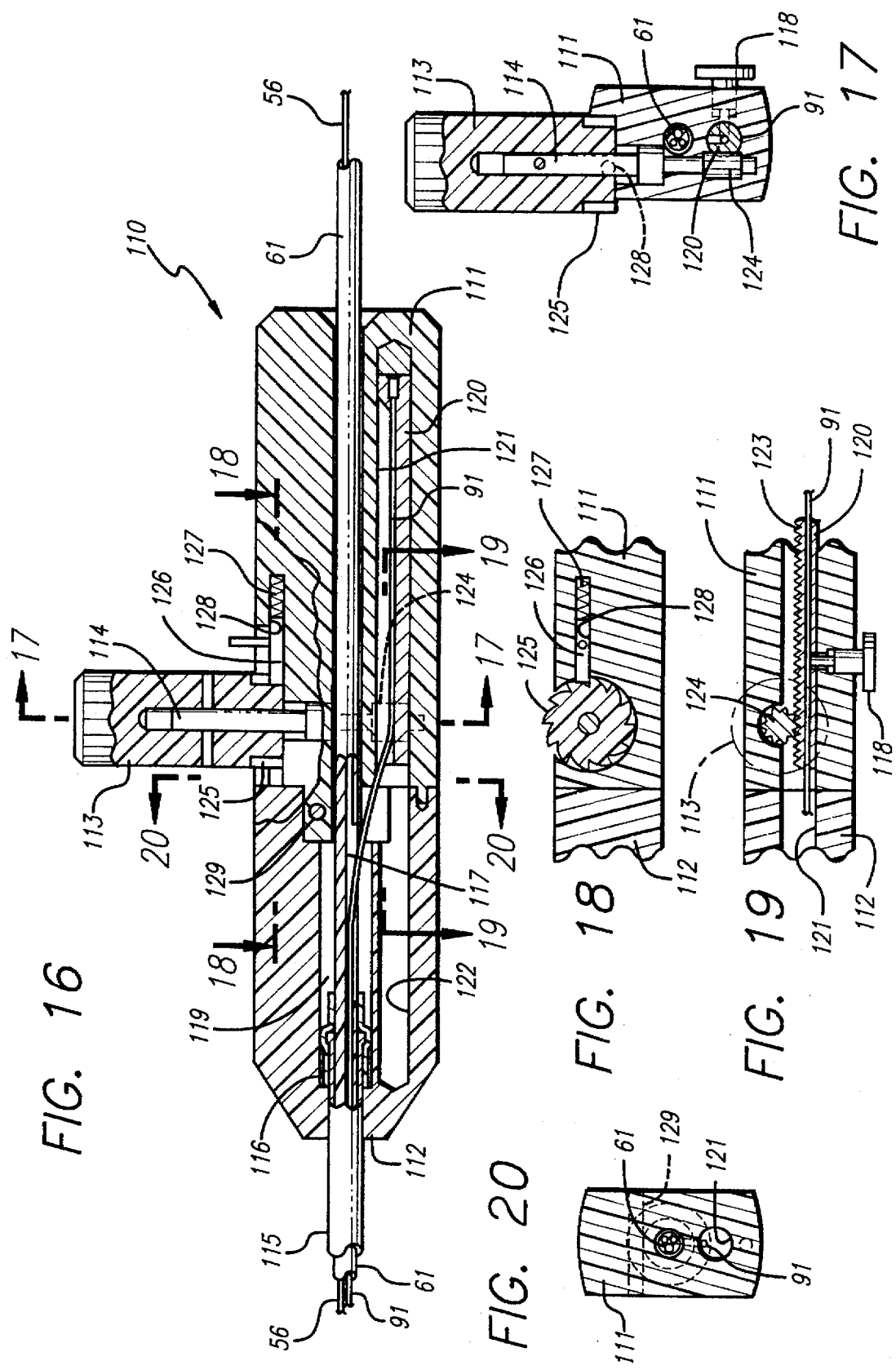

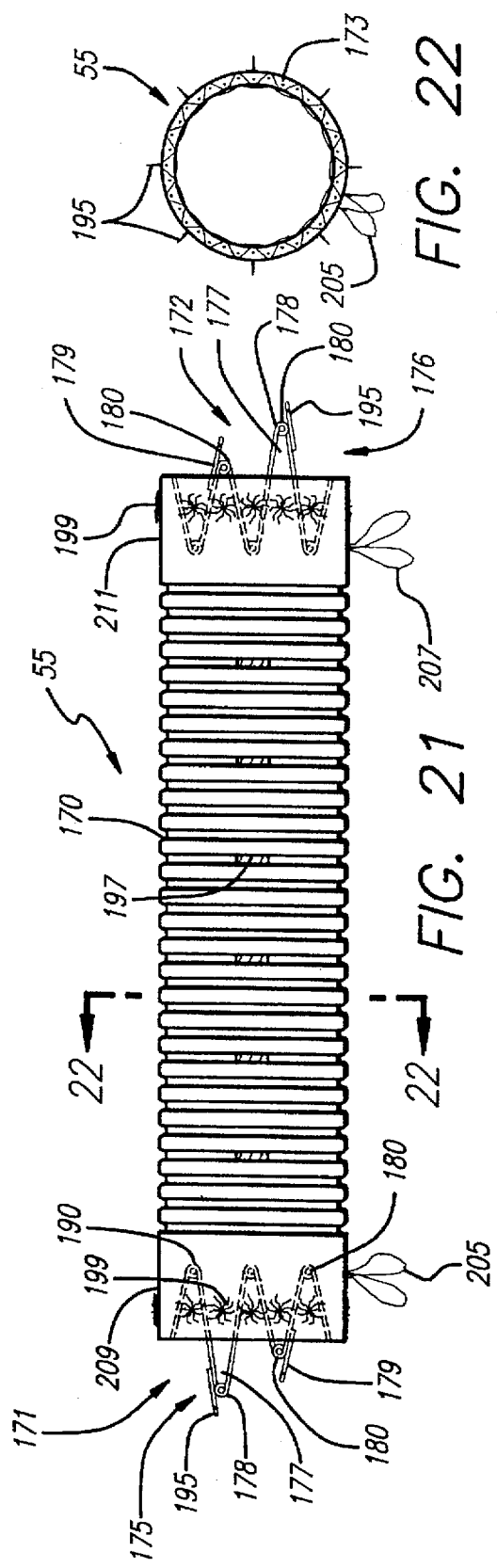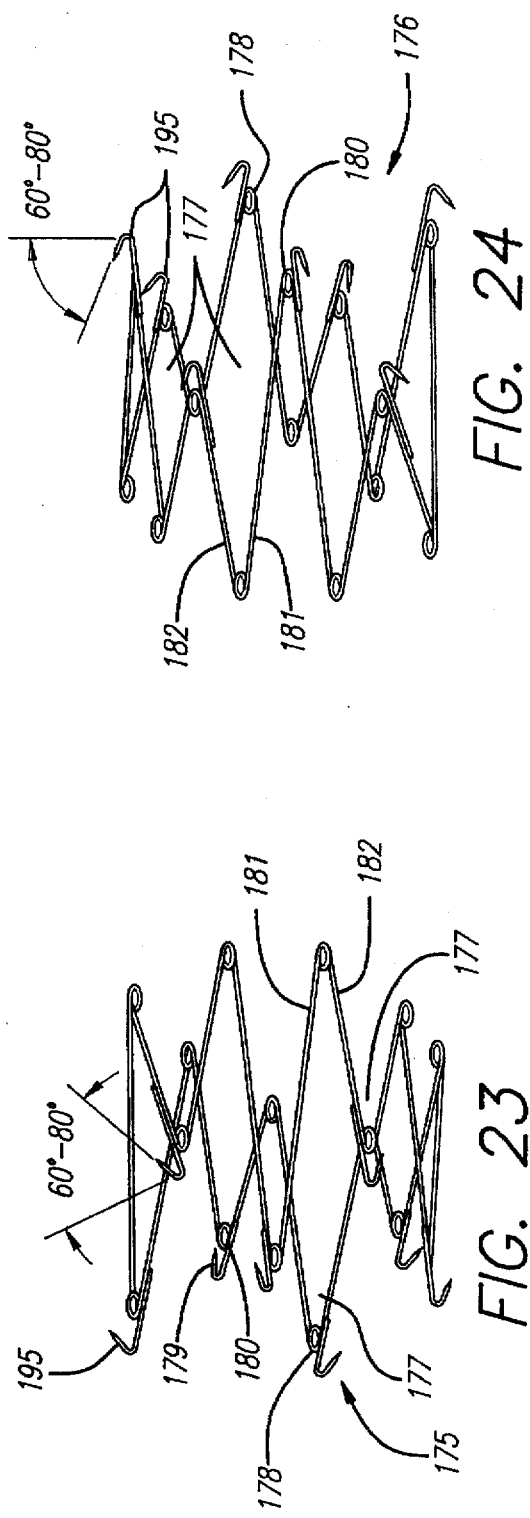

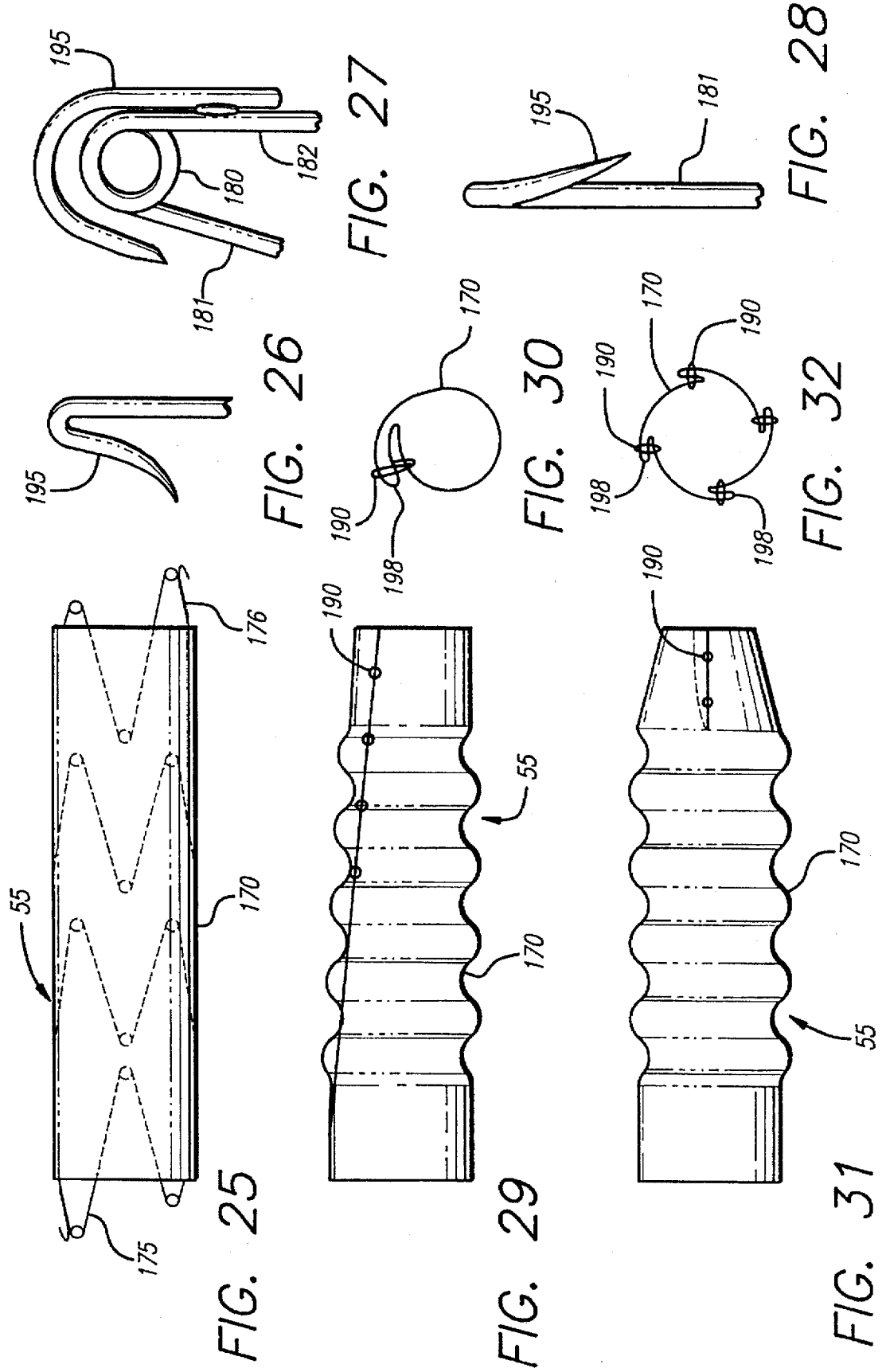

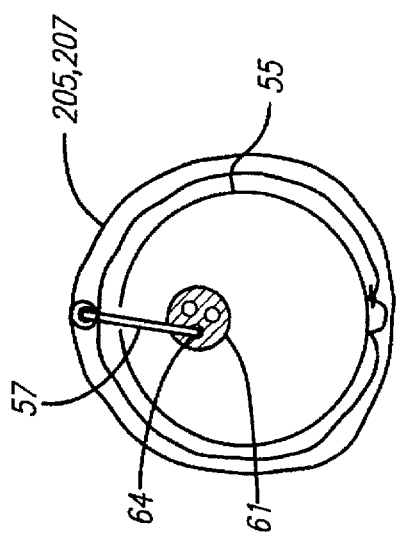
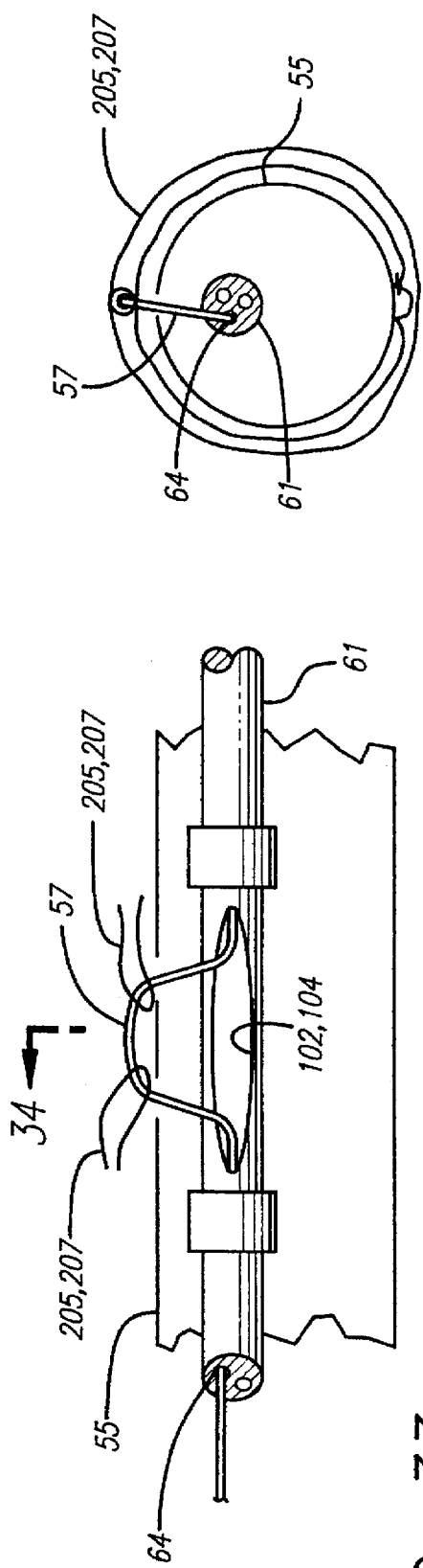
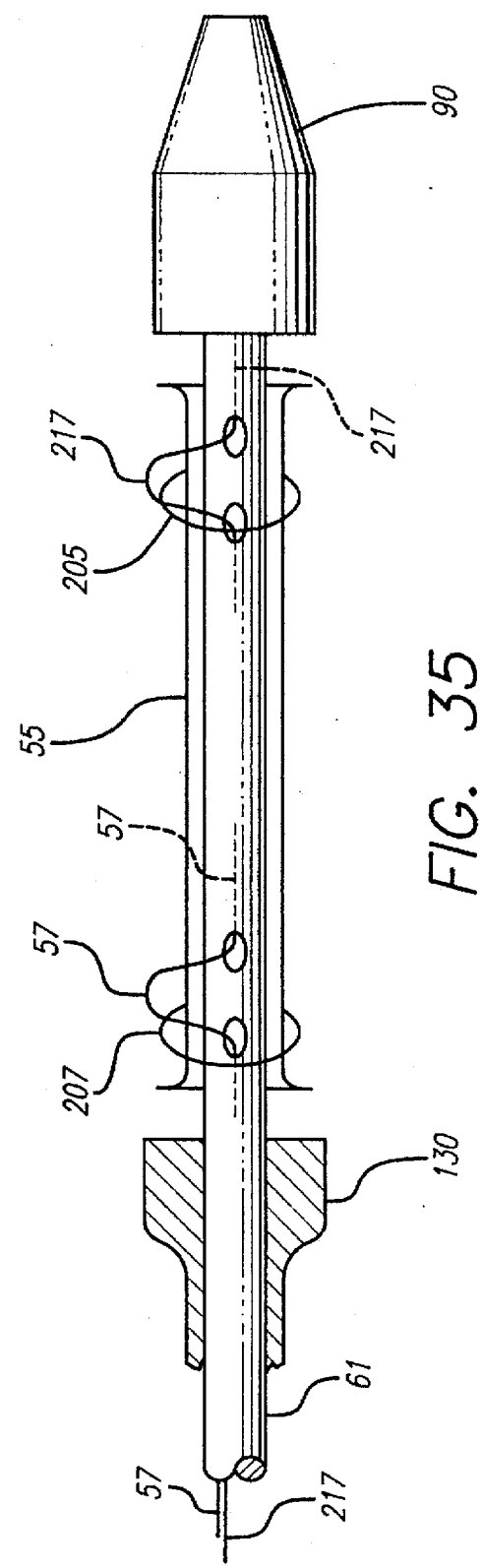

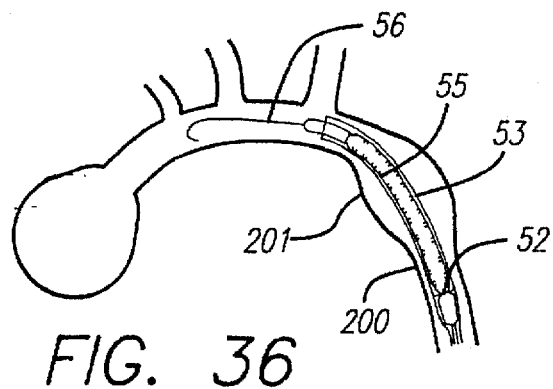
FIG. 36
FIG. 37
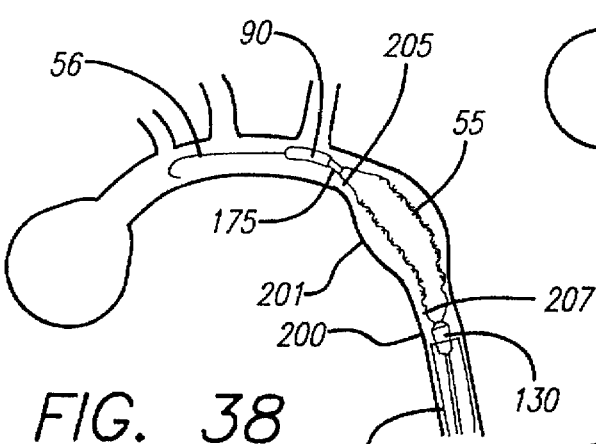
FIG. 38
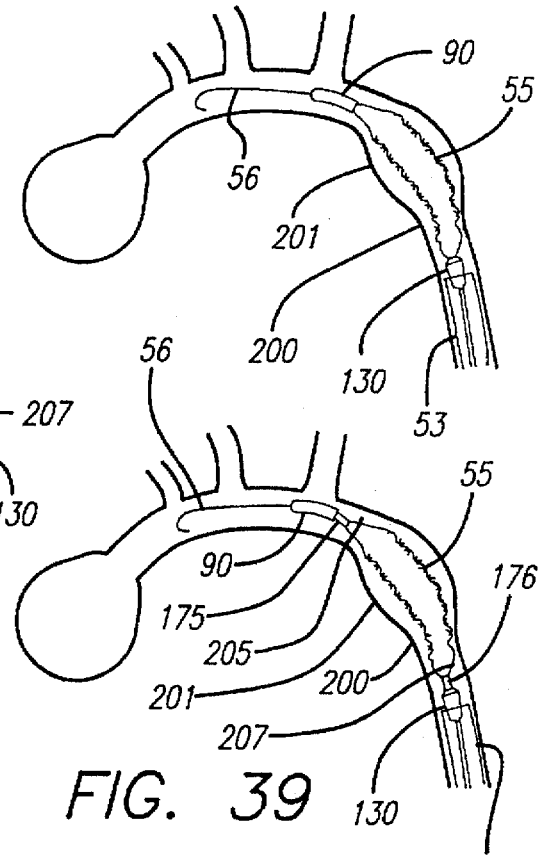
FIG. 39
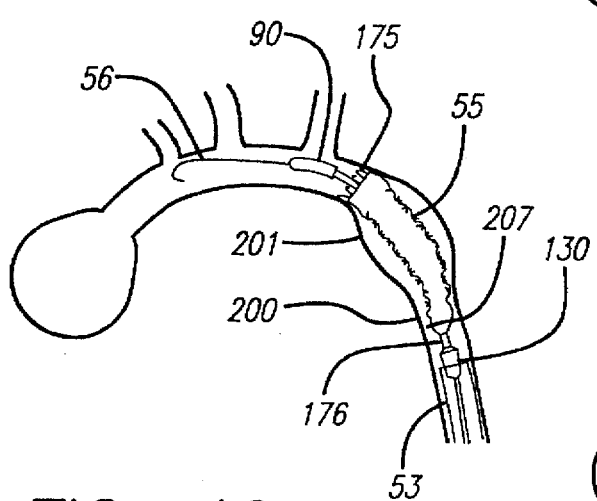
FIG. 40
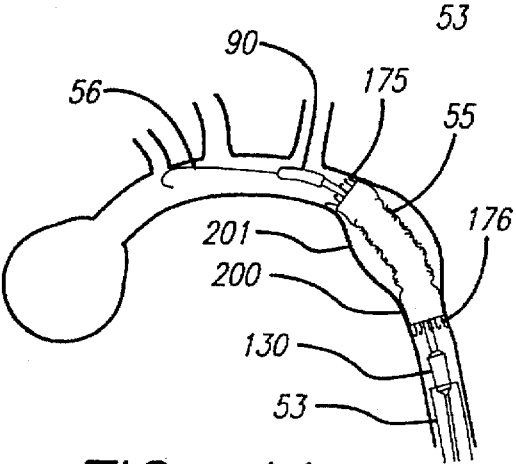
FIG. 41

THORACIC GRAFT AND DELIVERY CATHETER

This application is a continuation-in-part of application Ser. No. 102,576 filed Aug. 5, 1993, now abandoned, which is a continuation-in-part of application Ser. No. 553,530 filed on July 13, 1990, now U.S. Pat. No. 5,275,622, which is a continuation-in-part of application Ser. No. 166,093 filed on Mar. 9, 1988, now U.S. Pat. No. 5,104,399, which is a continuation-in-part of application Ser. No. 940,907 filed on Dec. 10, 1986, now U.S. Pat. No. 4,787,899 which is a continuation of application Ser. No. 559,935 filed on Dec. 9, 1983, now abandoned. The contents of each of these applications are hereby incorporated by reference.

BACKGROUND OF THE INVENTION

This invention relates to a system for implanting a prosthesis, and more particularly, to a delivery catheter for placing a graft having an attachment system within a corporeal lumen.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and, in turn, may be life-threatening. In some cases, the damaged lumen is repairable only with the use of a prosthesis such as an artificial vessel or graft. For repair of vital vessels such as the aorta, repair may be significantly life-threatening. Techniques known in the art which tend to minimize dangers to the patient include a procedure in which a graft resembling the natural vessel is placed within the diseased or obstructed section of the natural vessel.

More specifically, it is known within the art to provide a prosthesis for intraluminal repair of a vessel. In intraluminal vessel repair, the prosthesis is advanced intraluminally through the vessel to the repair site using a delivery catheter and deployed within the vessel so that the prosthesis traverses the diseased portion to thereby repair the vessel.

Generally speaking, varied concerns arise when repairing the different deteriorated disease that may affect a vessel. For instance, thoracic aneurysms differ from other aortic aneurysms in several respects. As may well be expected, due to their proximity to the heart, there are concerns specific to thoracic aneurysms that are not evident in the repair of other types of aortic aneurysms. Moreover, the size and shape of the thoracic aneurysms differ and are often more varied than other types of aortic aneurysms In particular, thoracic aneurysms are often close to what are typically called the great arteries, such as the left subclavian artery, or may be found to occur proximal to the celiac trunk. These lumens, which branch away from the thoracic region of the aorta, are critical to the body's circulatory system and carry high volumes of blood to various parts of the body. Consequently, these lumens generally cannot be occluded by a prosthesis used to intraluminally repair a thoracic aneurysm unless additional procedures are performed to bypass the occluded lumen.

In addition, thoracic aneurysms have diameters that are typically larger and have shapes perhaps more variable than other aortic aneurysms. The average neck diameter of thoracic aneurysms is on the order of 34–36 mm and the average length approximately 10 cm with a range of 5–16 cm. To complicate matters, due to the curvature of the aortic arch, the superior neck of thoracic aneurysms are often at a different angle from that of the inferior neck. Also, among the myriad of shapes they may take on, thoracic aneurysms may be fusiform in shape, or comprise giant penetrating ulcers.

Further, access to thoracic aneurysms through connecting arteries is limited and methods for implanting a prosthesis must take into account the physiology of and effects to the heart. Specifically, the femoral as well as the iliac arteries may be too narrow to pass a catheter for delivering a thoracic prosthesis or graft. Often, surgical repair of a thoracic aortic aneurysm requires thoracotomy. Also, it is not desirable for catheters delivering a thoracic graft to comprise a balloon since the use of the balloon to implant the graft would temporarily stop blood flow, thereby placing potentially dangerous loads upon the heart. Finally, due to high pressures existing in the area of a thoracic aneurysm, the attachment system of a graft for repairing a thoracic aneurysm must be sufficient to prohibit migration of the graft. It is also to be noted that there is typically a lack of calcification in the area of thoracic aneurysms. Consequently, the attachment systems of grafts for repairing thoracic aneurysms generally need not be placed within the lumen with forces overcoming such hardening of tissue.

Thus, what has been needed and heretofore unavailable is a graft and a delivery catheter system therefor, wherein the graft is designed specifically to repair thoracic aortic aneurysms and the delivery system functions to precisely position a graft within an aorta to thereby completely repair the thoracic aneurysm. The graft is to be configured to conform to the various possibilities of shapes of the thoracic aneurysm and to have an attachment system which effectively affixes the graft within the aorta. In addition, the delivery catheter is to effectively operate within the unique anatomical constraints of the thoracic portion of the aorta. The present invention accomplishes these goals.

SUMMARY OF THE INVENTION

Briefly, and in general terms, the present invention provides a new and improved graft and delivery catheter and a novel method for their use in repairing a lumen. The graft is configured for repairing a diseased condition of the lumen. The delivery catheter is configured to introduce the graft within or between vessels or corporeal lumens of an animal, such as a human, and to facilitate the deployment of the graft at the repair sites.

The present graft has a diameter that is larger than that of conventional grafts so that relatively larger lumens may be repaired and its walls are thinner to facilitate packing it within the delivery catheter. The attachment system of the present graft is expandable and is stiffer and has hooks with greater angles from radial than conventional attachment systems. Also, in addition to being secured to the ends of the graft, the attachment system is secured by its apices to the graft to prevent relative motion of the attachment system and graft. Further, the novel attachment system of the present graft enables it to self expand quickly and forcefully without the aid of a balloon catheter as well as enables it to securely hold the graft within lumens carrying high volume of blood.

The present delivery catheter includes structure for quickly deploying the graft within the lumen to be repaired. Further, by not employing a balloon catheter, the delivery catheter may be utilized to repair lumens located near the heart without placing undue stress on the heart and is configured for packing a larger diameter graft within the delivery catheter. Additionally, the delivery catheter is configured to hold the attachment systems affixed to the ends of the graft within capsules and by not placing the entire graft within a single capsule, larger diameter grafts may be packed within the delivery catheter. Moreover, the delivery catheter is longer which enables it to reach an aortic arch and employs a novel releasing system cooperating with the capsules which, in conjunction, operate to facilitate loading as well as deployment of the graft. The releasing system includes a release wire cooperating with releasable ties attached to the exterior of the graft to maintain the attachment systems of the graft in a collapsed configuration and to facilitate the expansion of the attachment systems so that they properly and quickly engage the walls of the lumen.

The present invention provides a prosthesis or graft for intraluminal placement in a fluid conducting corporeal lumen. The graft is hollow and has a pre-selected cross-section, length and wall thickness. The graft is deformable to conform substantially to the interior surface of the corporeal lumen or other body part to be repaired. The midsection of the graft may be crimped to resist kinking and facilitate placement accuracy and may comprise radiopaque markers attached along its length to help orient the graft using fluoroscopy or X-ray techniques. Tufts of yarn are sewn into the graft at its ends to facilitate healing and placement of the graft within the corporeal lumen. Preferably, the graft comprises woven polyester or another material suitable for permanent placement in the body such as PTFE. The superior and inferior ends of the graft are positioned within the corporeal lumen and the graft is configured such that it traverses the diseased or damaged portion of the vessel. To anchor the graft to the wall of the corporeal lumen, attachment systems are secured to the superior and inferior ends of the graft.

The preferred attachment system includes wall engaging members. The wall engaging members of the superior attachment systems are angled toward the inferior end of the graft. Similarly, the wall engaging members of the inferior attachment systems are angled toward the superior end of the graft. Specifically, the angles of both the superior and inferior wall engaging members are in the range of 60°–80° from radial. The wall engaging members of both attachment systems have sharp tips for engaging the corporeal lumen wall. The preferred attachment systems are formed into a staggered V-shape lattice or framework, the apices of which comprise helical torsion springs. The frame of the attachment systems allows for elastic radial deformation resulting in a spring-like effect when a compressed attachment system is allowed to expand as the graft is released from the capsules, and by having a high stiffness, they function to quickly and forcefully seat the graft within the lumen.

Preferably, the delivery catheter of the present inventor is flexible and includes an elongate cylindrical jacket overlaying a superior capsule assembly and an inferior capsule assembly, each of which are adapted to releasably retain an end of the graft. The superior capsule assembly further includes an elongated flexible conical-shaped or tapered nose cone adapted to facilitate the advancement of the delivery catheter through a patient's vasculature. Attached at the most proximal end of the inferior capsule assembly is an elongate outer shaft, comprising an inferior capsule catheter, which is adapted to receive a multi-lumen inner shaft. The lumens of the inner shaft are conduits for a guidewire, one or two release wires, an anti-elongation wire and a control wire that cooperates with the superior capsule assembly. Attached to the inner shaft and distal to the outer shaft/ inferior capsule assembly junction is a conical-shaped knob that cooperates with the superior capsule assembly. Also attached to the inner shaft is an anti-elongation wire that functions to minimize elongation of the inner shaft during deployment of the graft. The jacket is capable of moving relative to the rest of the catheter and thus can be withdrawn, thereby exposing the capsules and graft. Similarly, the capsules can be caused to move relative to the inner shaft and the structure attached thereto, which, in conjunction with the operation of the releasing system, thereby causes the deployment of the graft within a lumen. The length of the delivery catheter is sufficient for use in reaching the thoracic portion of the aorta and has a diameter suited for encasing a graft for use in repairing a thoracic aneurysm.

Deployment of the graft comprises a series of steps which begins with introducing the delivery catheter into the corporeal lumen using well known surgical techniques. The delivery catheter is manipulated so that the graft retained by the superior and inferior capsule assemblies is positioned at a desired location within the corporeal lumen. Once the graft is in the desired location, the jacket is retracted and the superior and inferior capsule assemblies are removed from the graft to expose the superior and inferior attachment systems of the graft. After this is accomplished, the releasing system is employed to thereby allow the attachment systems self-expand and seat the graft within the lumen.

Two methods are contemplated for placing the graft within a lumen. As a first step in each method, the jacket is moved proximally to expose the graft retained by the superior and inferior capsules. In the first method, the superior capsule assembly is moved distally to expose the superior end of the graft and the inferior capsule assembly is moved proximally to expose the inferior end of the graft. The releasing system is then employed to release the superior attachment system, thereby allowing the superior attachment system to affix the superior end of the graft within the lumen. Thereafter, the releasing system is employed to release the inferior attachment system to thereby allow the inferior attachment system to affix the inferior end of the graft within the lumen. In the second method, these steps are reordered so that the inferior end of the graft is first seated within the lumen and thereafter, the superior end is seated.

Other features and advantages of the present invention will become apparent from the following detailed description, taken in conjunction with the accompanied drawings, which illustrate, by way of example, the features of the invention.

BRIEF DESCRIPTION OF THE DRAWINGS

FIG. 1 is a top plan view of the delivery catheter and graft incorporating the present invention.

FIG. 2 is a top plan view of a an anti-elongation wire of the present invention.

FIG. 3 is a top plan view of a release wire of the present invention.

FIG. 4 is a top plan view of a guidewire to be used with the delivery catheter of the present invention.

FIG. 5 is a top plan view of an inner catheter assembly of the present invention.

FIG. 6 is a top plan view of a superior capsule assembly, control wire, hypotube and control wire handle assembly of the present invention.

FIG. 7 is a top plan view of an inferior capsule and capsule catheter of the present invention.

FIG. 8 is a top plan view of a capsule jacket assembly of the present invention.

FIG. 9 is a top plan view of a graft for use with the delivery catheter of the present invention.

FIG. 10 is a cross-sectional view taken along the line 10—10 of FIG. 1.

FIG. 11 is an alternate embodiment of the view depicted in FIG. 10.

FIG. 13 is an enlarged perspective view showing a presently preferred embodiment of the distal end of the control wire, superior cap insert, superior cap and nose cone.

FIG. 14 is an enlarged cross-sectional view of the superior capsule assembly.

FIG. 15 is a cross-sectional view taken along the line 15—15 of FIG. 14.

FIG. 16 is a partial cross-sectional view of the control wire and control handle mechanism of FIG. 1.

FIG. 17 is a cross-sectional view taken along the line 17—17 of FIG. 16.

FIG. 18 is a cross-sectional view taken along the line 18—18 of FIG. 16.

FIG. 19 is a cross-sectional view taken along the line 19—19 of FIG. 16.

FIG. 20 is a cross-sectional view taken along the line 20—20 of FIG. 16.

FIG. 21 is a partial cross-sectional view of the graft and attachment system of the present invention.

FIG. 22 is a cross-sectional view taken along the line 22—22 of FIG. 21.

FIG. 23 is an enlarged perspective view showing a superior attachment system.

FIG. 24 is an enlarged perspective view showing an inferior attachment system.

FIG. 25 is a perspective view showing an alternate embodiment of the graft.

FIG. 26 is an enlarged perspective view showing an alternate embodiment of the wall engaging members of the attachment system.

FIG. 27 is an enlarged perspective view showing an alternate embodiment of the wall engaging member of the present invention.

FIG. 28 is an enlarged perspective view showing another view of the alternate embodiment of FIG. 27.

FIG. 29 is a perspective view showing another embodiment of the graft.

FIG. 30 is a cross-sectional view of the graft depicted in FIG. 29.

FIG. 31 is a perspective view showing yet another embodiment of the graft.

FIG. 32 is a cross-sectional view of the graft depicted in FIG. 31.

FIG. 33 is a partial cross-sectional view of the delivery catheter and graft, illustrating a releasing system of the delivery catheter.

FIG. 34 is a cross-sectional view taken along the line of 34—34 of FIG. 33.

FIG. 35 is a partial cross-sectioned view of the delivery catheter and graft, illustrating another embodiment of the releasing system of the delivery catheter.

FIG. 36 is a partial cross-sectional view of the delivery catheter and graft positioned within the corporeal lumen.

FIG. 37 is a partial cross-sectional view of the delivery catheter and graft shown in FIG. 33, wherein the capsule jacket has been retracted proximally relative to the delivery catheter.

FIG. 38 is a partial cross-sectional view of the delivery catheter and graft shown in FIG. 34, wherein the superior capsule assembly has been removed from the superior end of the graft.

FIG. 39 is a partial cross-sectional view of the delivery catheter and graft shown in FIG. 35, wherein the inferior capsule has been removed from the inferior end of the graft.

FIG. 40 is partial cross-sectional view of the delivery catheter and graft shown in FIG. 36, wherein the release system has been used to facilitate emplacement of the superior attachment system within the corporeal lumen.

FIG. 41 is a partial cross-sectional view of the delivery catheter and graft shown in FIG. 37, wherein the release system has been utilized to facilitate emplacement of the inferior attachment system within the corporeal lumen.

DETAILED DESCRIPTION OF THE PREFERRED EMBODIMENTS

Figure 12:
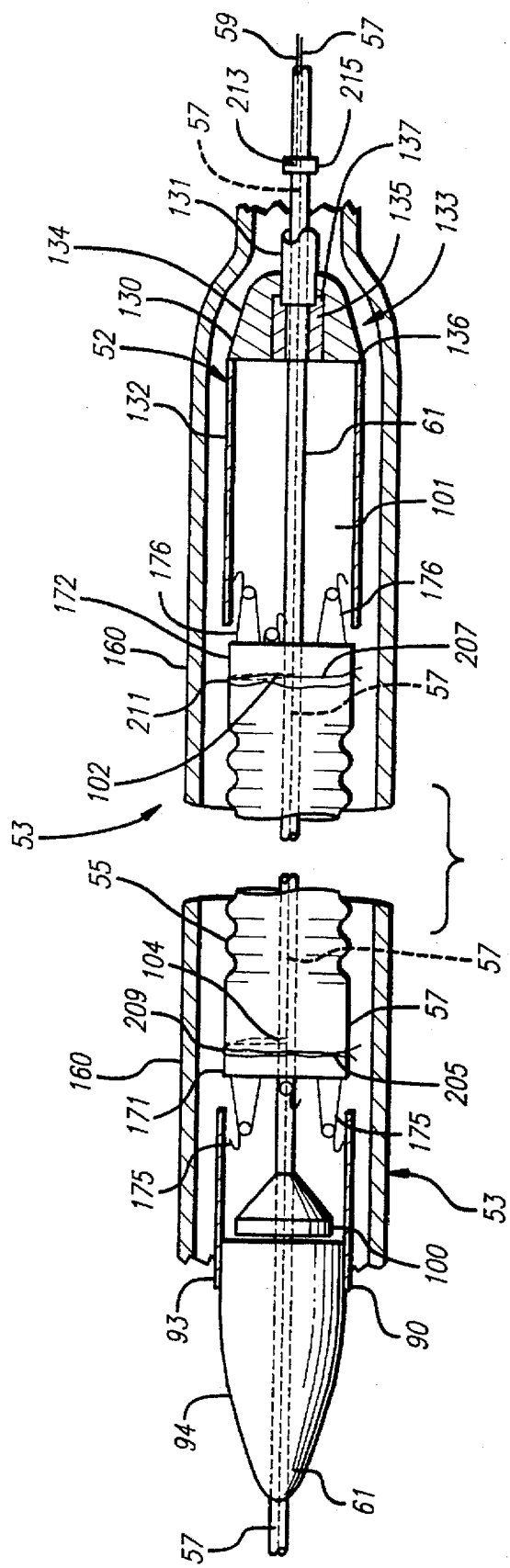
FIG. 12 is a partial cross-sectional view of the inferior capsule, superior capsule and capsule jacket assemblies and the anti-elongation wire, release wire and graft.

As is shown in the drawings and for purposes of illustration, the invention is embodied in a thoracic graft and a delivery catheter therefor. One of the novel features of the present invention is the attachment system of the graft which operates to securely affix the graft within a lumen without the aid of a balloon catheter. Another novel feature of the present invention is the releasing system which functions to release the attachment systems of the graft once the graft has been advanced within the vasculature of the patient to the repair site.

Generally, in the present invention, the graft is comprised of a monoluminal tubular member having superior and inferior extremities. Expandable attachment systems are secured to the superior and inferior ends of the tubular member. The attachment systems are provided with wall engaging members which are covered by the inferior and superior capsule assemblies. The delivery catheter includes a plurality of elongate components which are configured coaxially so that relative movement between them provides for deployment of the graft.

In more detail, the delivery catheter 50 is shown in FIGS. 1–8. As shown in FIG. 1, the delivery catheter 50 includes an inner catheter assembly 51, which is coaxially disposed within an inferior capsule catheter 52, which is coaxially disposed within the capsule jacket 53. Also disposed about the inner catheter is a superior capsule assembly 90. Attached to the inferior capsule catheter 52 is an inferior capsule assembly 130. The inferior capsule assembly 130 and the superior capsule assembly 90 are used to contain the attachment systems of the graft 55. A control wire assembly 54 (see FIG. 6) is coaxially disposed within one of a plurality of lumens of an inner shaft 61 included in the inner catheter assembly 51 and is configured to move the superior capsule assembly 90 in relation to the other components. In the preferred embodiment, the system is used as an over-the-wire device, such that the delivery catheter 50 is further configured with a lumen for a guidewire 56 (see FIG. 4). It is contemplated, however, that the system can also be used with a well known fixed wire delivery configuration.

Moreover, the delivery catheter 50 includes a release wire 57 (see FIG. 3). The release wire 57 comprises a portion of a releasing system of the delivery catheter 50. The release wire 57 is adapted to be disposed within one of the plurality of inner shaft 61 lumens and cooperates with structure attached to the graft 55 to maintain the attachment systems of the graft 55 in a collapsed configuration (see FIG. 12) as well as to facilitate the timely expansion of the attachment systems so that the graft 55 may be implanted in a lumen.

Preferably, the release wire 57 has a diameter of approximately 0.010 inches and a length on the order of 100 cm, so that its inferior end 77 may be manipulated by the operator yet be long enough to extend beyond the repair site. In a presently preferred embodiment, the inferior end 77 of the release wire 57 is attached to a rotating knob (not shown) so that when the knob is rotated, the release wire 57 wraps around the knob thereby causing it to move proximally relative to the other components of the deliver catheter 50. It is also contemplated that, in the alternative, the inferior end 77 of the control wire 57 is adapted to be gripped by the operator. The release wire 57 may be made from FEP coated nitinol.

Additionally, the delivery catheter includes an anti-elongation wire 59 (see FIG. 2). The anti-elongation wire 59 cooperates with the inner shaft 61 to prevent stretching of the inner shaft 61 during deployment of the graft 55 within the lumen. A superior end 79 of the anti-elongation wire 59 is attached to the inner shaft 61. An inferior portion 78 is similarly attached to the inner shaft 61. The anti-elongation wire 59 may be disposed within a lumen of the inner shaft 61 or may be positioned along side the inner shaft 61. Preferably, the diameter of the anti-elongation wire 59 is approximately 0.008 inches. In one presently preferred embodiment, the anti-elongation wire 59 is made from kevlar yarn but it can also be made of stainless steel.

As shown in FIG. 10, the inner shaft 61 is preferably configured with multiple lumens; however, the inner shaft 61 may be configured with a single or a plurality of lumens. A guidewire lumen 63 extends the length of the inner shaft 61. A release wire lumen 64 also extends the length of the inner shaft 61. A control wire lumen 65 is provided for a control wire 91 included in the control wire assembly 54 and also extends the length of the inner shaft 61. In an alternative embodiment, the inner shaft 61 also includes an anti-elongation lumen 66 extending its length (see FIG. 11). Additionally, as will be hereinafter discussed in more detail, the inner shaft 61 may include a plurality of reinforcing bands, low profile projections or bumps and slits.

The flexible elongate element of the inner shaft 61 is preferably formed of a material suitable for intraluminal use, such as crosslinked polyethylene tubing. The multi-lumen shaft 61 is preferably extruded to an outer diameter of 0.08 inches (2.03 mm). The guidewire lumen 63 has an inner diameter of 0.040 inches (1.02 mm). The release wire lumen 64 and the control wire lumen 65 each have a diameter of 0.022 inches (0.56 mm) but may range from 0.015 to 0.030 inches (0.381–0.762). The outside diameter may range from 0.035 to 0.1 inches (0.889–2.54 mm). In the embodiment of the inner shaft 61 that includes the anti-elongation lumen 66, the anti-elongation lumen 66 may have a diameter of at least 0.008 inches. The inner shaft 61 may vary in length to suit the application, for example, from 50–150 cm.

As shown in FIGS. 5 and 12, a conical-shaped knob 100 is affixed to inner shaft 61. As will be developed below, the conical-shaped knob 100 cooperates with the graft 55 and superior capsule assembly 90 to facilitate emplacement of the graft 55 within a lumen. The inner shaft 61 also includes two release wire notches 102, 104 which provide a space for the release wire 57 to exit and reenter the release wire lumen 64. By providing such a space, the release wire 57 can exit the inner shaft 61 and be placed into engagement with the structure attached to the graft 55 which function to control whether the attachment systems of the graft are in their collapsed or expanded configuration. In one presently preferred embodiment, each notch 102, 104 is flanked by reinforcing bands (not shown) which add structural reinforcement to the inner shaft 61 to prevent elongation of the notches 102, 104 as well as low profile bumps (not shown) formed on the inner shaft 61 which aid in keeping the reinforcing bands in place. Preferably, the material of the reinforcing bands is selected so that they perform as radiopaque markers. Further, additional bumps (not shown) may be formed on the inner shaft 61 to cooperate with the superior capsule assembly 90 to limit its proximal and distal movement.

The delivery catheter also includes the control wire assembly 54, which is shown in FIGS. 1 and 6. The distal end of the control wire assembly 54 consists of the superior capsule assembly 90. As shown in more detail in FIGS. 13–15, the superior capsule assembly 90 may comprise a control wire 91 secured within a superior cap insert 96 that is placed within a superior cap 92. The superior cap 92 includes a threaded male portion that is received in a nose cone 94 having a threaded female portion. The nose cone 94 is flexible and has an elongated conical or tapered shape adapted to facilitate advancement of the delivery catheter 50 through a patient's vasculature. A hollow superior capsule 93 is secured to the superior cap 92 and coaxially surrounds the control wire.

As shown in FIG. 12, the conical-shaped knob 100 is secured to the inner shaft 61 and may be positioned within superior capsule 93 at a location adjacent and proximal to the superior cap 92. As the control wire is moved in a longitudinal manner, the superior end of the control wire 95, the superior cap insert 96, the superior cap 92, the nose cone 94 and the superior capsule 93 each move as a single assembly (see also FIG. 14).

The nose cone 94 may be made from PEBAX and the superior cap 92 may be formed from polycarbonate or other suitable material for insertion through the body lumen. The nose cone 94 is formed with a bore 104 of approximately the same diameter as the outer diameter of the inner shaft 61. Similarly, the superior cap insert 96 may be formed of the same material as the superior cap 92, wherein the superior cap insert 96 is provided with a bore 105 for receiving the inner shaft 61. The superior cap 92 is further provided with a recess 106 or other means for receiving the superior end of the superior capsule 93. The superior capsule 93 is preferably formed of stainless steel, but may be formed of other suitable biocompatible material, such as a nickel titanium. The superior cap recess 106 is angled to allow crimping of the superior capsule 93 to the superior cap 92.

The outside diameter of the superior capsule 93 may range from 4–9 mm and is preferably 0.289 inches (7.3 mm) in outer diameter and 0.276 inches (7.01 mm) inner diameter. The length of the superior capsule 93 is approximately 0.87 inches (22 mm).

FIGS. 13–15 show a presently preferred embodiment of the superior capsule assembly 90. In this embodiment, the control wire 91 is threaded through an opening 107 in the superior cap insert 96. A longitudinal slot 109 is cut out in the inner shaft 61 to expose the control wire lumen 65. The control wire is formed in a U-shaped bend over the opening in the superior cap insert and is configured to slide within the slot and in the inner shaft lumen 65. The distal end of the control wire 95 resides in the superior cap insert 96. This configuration allows the superior cap assembly to move axially along the inner catheter shaft. The U-shaped bend of the control wire through the superior cap insert, however, prevents the superior cap assembly from rotating in relation to the inner catheter shaft. As described above, the superior cap insert is firmly secured within the superior cap.

It is to be understood that other embodiments of the superior capsule assembly are contemplated. For instance, the control wire may be configured to pass through the superior capsule assembly, by way of the inner shaft lumen 65, and be attached at a superior end of the superior cap. Irrespective of the embodiment, however, it is contemplated that the control wire causes relative movement of the superior capsule assembly and the inner shaft.

As shown in FIGS. 16–20, a handle assembly 110 is secured to the proximal end of the control wire 91. The handle assembly comprises a proximal body 111, a distal body 112, a control knob 113 with rotating shaft 114 and a hypotube 115. The two handle body parts have a central bore 119 for receiving the inner shaft 61. A retaining pin 129 may be used to secure the two pieces of the handle body together. It is also contemplated that the handle assembly 110 include one or more release wire knobs (not shown), each having a rotating shaft adapted to be attached to a release wire. Upon rotation of a release wire knob, it is contemplated that the release wire wraps around the rotating shaft to thereby cause the release wire to retract.

The hypotube 115 is coaxially disposed over the inner shaft 61 and extends distally from the central bore 119 in the distal handle body 112. The proximal end of the hypotube is secured to the inner shaft 61 approximately one centimeter proximal from the distal end of the distal handle body by means of a polyethylene sealing tube 116 which is heat shrunk over the proximal end of the hypotube. An adhesive may be used to fix the distal handle body to the hypotube.

Hypotube 115 consists of a rigid thin wall tube formed of a suitable material such as stainless steel. The hypotube has a length of about 55 centimeters and has an outside diameter of 0.095 inches (2.41 mm) and an inside diameter of 0.087 inches (2.21 mm). When a crimped graft 55 is used, the hypotube may have marker bands (not shown) at predetermined positions distal of the control handle body 112. The marker bands facilitate the correct positioning of the inferior end of the graft.

Referring to FIG. 16, the control wire 91 resides in an inner shaft lumen 65 and extends from the superior capsule assembly 90 to an aperture 117 located in the lumen just proximal of the proximal end of the hypotube 115. The control wire preferably consists of an elongate solid flexible stainless steel wire having a lubricating coating, such as fluorinated ethylene-propylene (FEP). The coated control wire is about 0.02 inches (0.508 mm) in diameter, providing sufficient strength to move the inferior capsule assembly without buckling or kinking.

The proximal end of the control wire 91 is disposed within a retaining rack 120, approximately six centimeters long and having a central bore to secure the control wire. The proximal end of the retaining rack 120 is slidably disposed within a longitudinal guiding slot 121 in the proximal handle 111. Similarly, the distal end of the retaining rack 120 is slidably disposed within an longitudinal slot 122 in the distal handle body 112.

The retaining rack 120 is configured with teeth 123 along a longitudinal edge which engage a pinion or gear 124. The pinion is attached to a lower end of the rotating shaft 114. The upper end of the rotating shaft is secured within the control knob 113 such that rotation of the control knob rotates the gear and in turn moves the retaining rack longitudinally within the guiding slots. Longitudinal movement of the retaining rack causes longitudinal movement of the proximal end of the control wire 91, causing like longitudinal movement of the distal end 95 of the control wire and of the superior capsule 93. As shown in FIGS. 17 and 19, a locking screw 118 is configured to fix the retaining rack in place. The locking screw ensures that the control wire and superior capsule will not move even if torque is applied to the control knob.

At the base of the control knob 113 is a locking gear 125 which has curved teeth. The curved teeth engage a locking pin 126 biased by a locking spring 127 disposed within a recess 128 in the upper surface of the proximal body 111 of the control handle 110. The configuration of the curved teeth allows the control knob to turn in only one direction while the locking pin engages the locking gear. When the locking pin is moved to compress the locking spring, then the control knob may be turned in either direction. The locking gear is preferably molded as part of a plastic control knob, but may be a separate mechanism secured to the base of the control knob.

As shown in FIGS. 1 and 7, the inferior capsule catheter 52 consists of an inferior capsule assembly 130 secured to the distal end of a flexible elongate outer shaft 131 formed of a suitable plastic material such as polyether block amide available under the trademark "PEBAX", available from Atochem Polymers, Glen Rock, N.J. The outer shaft member 131 is of a suitable length as, for example, 40 to 100 centimeters and preferably approximately 85 centimeters for the thoracic aortic artery. The outer shaft has a preferred outside diameter of 0.187 inches (4.75 mm) and an inside diameter of 0.125 inches (3.175 mm). The outer shaft can be produced in a certain color such as blue. To render the outer shaft radiopaque under x-rays, its material of construction may contain a radiopaque material, such as twenty percent by weight of bismuth subcarbonate or barium sulfate. The outer shaft may have markings or bands distal of the wye adapter 145 at predetermined positions to indicate capsule jacket retraction and locking points.

The inferior capsule assembly 130 has an inferior capsule 132 mounted on the distal extremity of the outer shaft member 131. The inferior capsule has a preferred diameter ranging from 4 to 9 millimeters, which may be configured to accommodate different size grafts. The length of the inferior capsule 132 is approximately 0.709 inches (18 mm). The inferior capsule is configured to match the size of the superior capsule assembly 90. The inferior capsule is preferably made of stainless steel or similar impermeable and rigid, or semi-flexible material. The outer shaft member also serves as a shaft for advancing the inferior capsule, as hereinafter described. Thus, the outer shaft member should have a diameter which is less than that of the inferior capsule.

Referring to FIG. 12, the inferior capsule 132 is secured to the distal extremity of the outer shaft member 131 by means of a capsule adapter assembly 133. The capsule adapter assembly comprises a housing 134 and an inner sleeve 135, which may be constructed from polycarbonate. The capsule adapter housing distal extremity 136 is secured in the proximal extremity of the capsule, for example, by crimping, by using a press fit swaging or an adhesive such as a cyanoacrylate ester. The capsule adapter housing distal extremity may be angled to facilitate securing the housing to the inferior capsule.

The proximal extremity of the capsule adapter housing 134 is secured to the distal extremity of the outer shaft member 131 by means of an cyanoacrylate ester adhesive, or other suitable means. To facilitate a mechanical lock, the outer shaft distal extremity is molded to form a flange 137, wherein the capsule adapter housing is configured so as to close around the flange. The capsule adapter housing is further provided with a recess for receiving the capsule adapter inner sleeve 135. The inner sleeve is provided with a bore of a suitable diameter so as to allow the inner shaft 61 to reside therein.

A wye adapter 145 (see FIG. 7) is secured to the proximal extremity of the outer shaft member 131 of the inferior capsule catheter 52. The central arm 146 of the wye adapter is connected to a Touhy Borst adapter 147 which tightens around the guiding member 115 disposed in the central arm of the wye adapter. The side arm 148 of the wye adapter has a stop cock 149 mounted therein which is movable between open and closed positions. The stop cock is provided with a Luer fitting 150 which is configured to accept a syringe for injecting a radiopaque contrast. Air may be purged from the capsule jacket assembly 53 by injecting fluid through the Luer fitting. The injection fluid will exit purge ports 151 and 152, thereby filling the capsule jacket assembly with injection fluid. The Luer fitting may be attached to a saline drip line during the operative procedure.

Referring to FIGS. 1, 8 and 12, the capsule jacket assembly 53 is slidably disposed coaxially over the inferior capsule catheter 52 and the inner catheter assembly 51. The capsule jacket assembly is comprised of a main jacket 160, and a locking connector 162. The main jacket diameter changes at a point approximately 15 centimeters from the distal end 163, depending on the length of the graft 55. The main jacket flares to an expanded diameter to cover the graft 55, the inferior capsule 132 and the superior capsule 93. The proximal ends of the jacket may be secured to the jacket adapter 164 of the locking connector by mechanical means and by adhesive.

When the capsule jacket assembly 53 is in its most distal position, the distal end 163 of the capsule jacket extends to cover at least a portion of the superior capsule assembly 90. Similarly, the capsule jacket locking connector 162 is thereby positioned proximal to the inferior capsule catheter purge port 151. Prior to insertion into the lumen, locking ring 165 (not shown) is turned to hold the capsule jacket assembly firmly in place, thereby maintaining a smooth transition surface along the length of the delivery catheter 50 which resides in the body vessels. When the locking ring is released, the capsule jacket assembly may be moved to a furthermost proximal position, wherein at least a portion of the inferior capsule assembly 130 is exposed. Thus, the locking connector is positioned just distal to the capsule catheter wye adapter 145. The locking ring may be tightened at any intermediate position to firmly secure the capsule jacket assembly at the desired location. In addition, a radiopaque marker 166 is provided at the distal end of the main jacket to facilitate proper linear positioning of the capsule jacket.

As shown in FIGS. 1 and 9, the present invention includes an expandable intraluminal vascular graft 55 for implanting in a body vessel. Referring to FIG. 21, the graft consists of a deformable tubular member 170 which is provided with superior end 171, inferior end 172 and a cylindrical or continuous wall extending between the superior and inferior ends 171, 172 of the graft 55. A midsection of the tubular member of the graft 55 is crimped to resist kinking. Although a standard size crimp may be used, it is preferred to make the crimps radially deeper and less numerous than produced from standard crimping techniques. Having a sparsely crimped profile also reduces the elongation properties of the graft 55. Moreover, a sparsely crimped graft 55 is easier to pack into the capsule jacket than a standard crimped graft. The low bulk and low elongation of the crimped graft further allows that the graft 55 may be packed into a smaller diameter capsule jacket. Additionally, the low crimp elongation factor allows for a higher degree of placement accuracy.

The crimps of the thoracic graft 55 may have a configuration approximating a square wave wherein the raised portion has an approximate width of 1.5 millimeters and the valley has an approximate width of 0.7 millimeters. The resulting crimp pitch is then preferably 2.2 millimeters. Further, the crimped graft 55 of the present invention is configured with crimps having raised portions that are preferably approximately 1.2 millimeters deep. So configured, the graft 55 will maintain its high flexibility even under arterial pressures of over one hundred mm Hg within the corporeal lumen and the crimps will function to resist kinking. Also, by being so configured, radiopaque markers may be sewn within the selected valleys.

The tubular member may have a length in the range of 7 to 15 centimeters. The tubular member may have a diameter of 30 to 40 mm. The continuous wall can be woven of any surgical implantable material such as polyethylene terephthalate (PET or polyester), but can be made of other materials such as PTFE. It is contemplated that the wall thickness be approximately 0.005 to 0.009 inches (0.127 to 0.229 mm), thinner than most conventional woven grafts. In order to prevent unraveling of the woven material at the ends, the ends can be melted with heat to provide a small melted bead of material on each end.

As shown in FIG. 21, a segment of polyester yarn 199 or similar material is used to produce a thrombogenic surface to improve blood clotting along the inferior and superior ends of the main tubular member 170. The filaments of the yarn segment are teased apart to increase the embolization area. The yarn segment is sutured to the wall 173 of the graft between one or more of the vees 177 of the superior and inferior attachment systems 175, 176. Other modifications may be made as to the location of the fuzzy yarns to produce a similar result. Likewise, the graft may be made of velour or terry to similarly occlude blood flow around the outside of the ends of the graft adjacent the attachment system and to enhance adhesion of the graft to the aorta.

Referring to FIG. 21, an expandable attachment system 175 is secured adjacent the superior end 171 of the tubular member 170. Similarly, an expandable attachment system 176 is secured adjacent the tubular member's inferior end 172. Each attachment system serves to yieldably urge the tubular member from a first compressed or collapsed position to a second expanded position and provides a fluid tight seal between the graft 55 and the corporeal lumen wall. Each attachment system is formed of a plurality of vees 177 with the outer apices 178 and inner apices 179 of the vees being formed with helical torsion springs 180 to yieldably urge the long legs and short legs of each of the vees outwardly at a direction approximately at right angles to the plane in which each of the vees lie.

As shown in more detail in FIGS. 23 and 24, the superior and inferior attachment systems 175, 176 are comprised of a single piece of wire which is formed to provide the vees 177 and also to define the helical torsion springs 180 between the legs 181 and 182. The two ends of the single piece of wire can be welded together in one of the legs to provide a continuous spring-like attachment system and is approximately 30 mm long. In the construction shown in FIGS. 23 and 24, it can be seen that the attachment systems have apices lying in four longitudinally spaced-apart parallel planes which are spaced with respect to the longitudinal axis of the tubular member 170. The apices lying in each plane are staggered to provide for the minimum profile when the attachment systems are placed in its collapsed condition.

The superior and inferior attachment systems 175 and 176 are secured to the superior and inferior ends 171 and 172, respectively, of the tubular member 170 by suitable means such as a polyester suture material 190. In an alternate embodiment, however, it is further contemplated that the center section of the graft be supported by one or more self-expanding attachment systems stacked end to end. (See FIG. 25). As shown in FIG. 21, the suture material is used for sewing the attachment systems onto the wall 173 of the tubular member. The suture material runs along each of the legs or struts 181 and 182 and through apices 178 and 179 to firmly secure each leg to the graft and to keep outer edge of the graft 55 from sliding medially along the attachment system. The inferior attachment system 176 may be attached to the inferior end 172 of the graft 55 in a similar manner. The furthest extending apices protrude approximately 9 mm beyond the ends of the graft and it is contemplated that the portion of the attachment system affixed to the graft extend approximately 25 mm from the ends of the graft toward its center. In a presently preferred embodiment, the attachment systems 175, 176 may be attached to the graft 55 so that the bottom of the inner apices 179 are positioned adjacent the ends 171, 172 of the graft 55. By so positioning the attachment systems 175, 176, the fluid tight seal between the graft 55 and vessel wall may be enhanced.

As shown in FIGS. 22–24, wall engaging members 195 are preferably secured to near the center of the legs 181, 182 by suitable means such as welding. The wall engaging members are secured near the center of the legs 181, 182 because the least amount of stress exists at the center of the legs 181, 182. Consequently, the fatigue life of the weld or other securing means is optimized. The wall engaging members are configured to extend beyond the apices 178, 179 approximately 2 mm and have a diameter ranging from 0.015 to 0.025 inches and a length from 2 to 5 millimeters. The wall engaging members are preferably sharpened to provide conical tips, and should have a length which is sufficient for the tip to penetrate into and perhaps through the corporeal lumen wall. There may be eight wall engaging members 195 per attachment system, one extending beyond each inner and outer apex 178, 179, or there may be four wall engaging members 195 per attachment system, wherein a wall engaging member extends beyond each outer apex 178. It is also contemplated that the hook portion of the wall engaging members, instead of being straight, be curved radially outward to facilitate insertion into the wall of the lumen being repaired (See FIG. 26). Further, the wall engaging members may be affixed to a strut so that the hook portion is substantially perpendicular to the plane in which the apex resides (FIGS. 23 & 24) or the hook may be routed over the apex, having its end curved radially outward so as to keep a low radial profile (FIG. 27 & 28).

The superior and inferior attachment systems 175, 176 and the wall engaging members 195 secured thereto are formed of a corrosion resistant material which has good spring and fatigue characteristics. One such material found to be particularly satisfactory is "ELGILOY" which is a cobalt-chromium-nickel alloy manufactured and sold by Elgiloy of Elgin, Ill. The wire can have a diameter ranging from 0.016 to 0.020 inches. For example, 0.020 inch diameter wire for the frame and wall engaging members may be used in the larger grafts of 36 to 40 millimeters diameter.

It has been found that the spring force created by the helical torsion springs 180 at the apices 178 and 179 is largely determined by the diameter of the wire. The greater the diameter of the wire, the greater the spring force applied to the legs 181 and 182 of the vees. Also, the longer the distances are between the apices, the smaller the spring force that is applied to the legs. It therefore has been desirable to provide a spacing between the outer extremities of the legs of approximately thirty millimeters, although smaller or larger distances may be utilized.

To facilitate securing the graft 55 in the corporeal lumen, the wall engaging members 195 of the superior attachment system 175 and inferior attachment system 176 may be angled with respect to the longitudinal axis of the tubular member 170. The wall engaging members face outwardly from the tubular member to facilitate holding the graft in place (See FIGS. 21–24). Preferably, the wall engaging members on the superior attachment means are inclined from the longitudinal axis and toward the inferior end of the graft 172 by 60° to 80° from radial. Likewise, the wall engaging members of the inferior attachment system may be inclined towards the superior end of the graft 175 by 60° to 80° from radial. By angling the wall engaging members so that they resist the force of the blood flow, the implanted wall engaging members oppose migration of the graft.

The helical torsion springs 180 placed at the apices 178 and 179 serve to facilitate compression of the graft 55 to place the superior and inferior attachment systems 175 and 176 within the capsule assemblies 90 and 130, as hereinafter described. The compression of the graft may be accomplished by deformation of the helical torsion springs to just beyond their elastic limit, thereby having a small component within the plastic range. Placing the apices in different planes and staggering or offsetting the wall engaging members 195 and 196 significantly reduces the minimum compressed size of the attachment systems. Having the apices in different planes also helps to prevent the wall engaging members from becoming entangled with each other or with the apices. The natural spring forces of the helical torsion springs serves to expand the graft to its expanded position as soon as the attachment system is released. Significantly, the spring forces of the attachment system of the graft 55 are such that the graft is securely attached within the lumen without the aid of a balloon catheter.

The graft 55 includes releasable ties 205, 207 attached to its exterior near the superior and inferior ends 171, 172 of the graft 55 respectively. The releasable ties 205, 207 cooperate with the release wire 57 of the delivery catheter 50 to load the attachment systems 175, 176 of the graft 55 within the inferior and superior capsules assemblies 90, 130 and to subsequently emplace the graft 55 within a corporeal lumen. As shown in FIG. 22, each releasable tie 205, 207 consists of a single thread that is attached at its midsection to the graft 55 so that a majority of the ties 205, 207 reside exterior to the graft 55 and configured into two loops. The loops are wrapped around the graft 55 and are placed into engagement with the release wire 57 by threading the release wire through each of the loops respectively. In the alternative, the ties 205, 207 can be looped around the release wire 57. Thereafter, the ends of the ties 205, 207 are pulled tight to collapse the attachment systems 175, 176 and are then stitched to the graft 55 and knotted.

It is to be noted that the ties 205, 207 can be threaded through the portions of the sutures which reside on the exterior of the graft and which secure the attachment systems to the graft 55. By doing so, when the release wire 57 is removed from engagement with the ties 205, 207, they are conveniently restrained from interfering with the expansion of the attachment systems. Further, due to the relative small size of the loops formed in the ties 205, 207, upon expansion of the attachment systems, they are removed from contacting the attachment systems. Moreover, by so configuring the ties 205, 207, they are kept out of the way of blood flow and are, therefore, made unavailable for occluding the vessel or causing the formation of unwanted blood clots. The ties 205, 207 may be made from braided polyester or nylon suture or any other material having similar properties.

In order to engage the releasable ties 205, 207, the release wire 57 is configured to pass through the walls of the graft 55. Since the graft 55 is contemplated to be woven, it comprises warp and weft yarns which are separated to allow passage of the release wire 57 through the walls of the graft 55. A superior passageway 209 is provided by separating warp and weft yarns located near the superior end 171 of the graft 55. Similarly, an inferior passageway 211 is provided by separating warp and weft yarns located near the inferior end 172 of the graft 55. In a presently preferred embodiment, each of the passageways 209, 211 consist of two sets of closely spaced-apart warp and weft yarns which are individually separated to allow passage of the release wire 57 through the walls of the graft 55, wherein one of the two sets of warp and weft yarns serves as an exit and the other as an entrance. In an alternate embodiment, each of the passageways 209, 211 consist of one set of warp and weft yarns that is separated to thereby provide both an exit and entrance for the release wire 57 through the graft walls.

In other embodiments, the releasable ties 205, 207 maybe passed through the graft 55 in order to be placed into engagement with the release wire 57. Further, the releasable ties 205, 207 may be configured so that eyes which are adapted to receive the release wire are knotted into each end of the ties. Additionally, it is also contemplated that, rather than passing the release wire 57 through each loop of each releasable tie 205, 207, the release wire 57 may be passed through only one loop of each releasable tie and the other loop of each releasable tie is placed around the first loop of the releasable tie receiving the release wire in order to provide a cooperating system for compressing the attachment systems 175, 176.

The graft 55 preferably contains radiopaque markers means for locating the graft 55 and for detecting any twisting of the graft 55 during deployment. The radiopaque marker means takes the form radiopaque markers 197 affixed along the crimped midsection of the graft and within the valleys comprising the crimped portion. The radiopaque markers are made of a suitable material such as a platinum tungsten alloy wire of a suitable diameter such as 0.004 inches (0.102 mm) which is wound into a spring coil having a diameter of 0.4 inches (1.0 mm). The radiopaque markers are secured to the tubular member 170 by sutures 199, using the same material to secure the attachment systems to the graft.

Referring also to FIG. 21, the radiopaque markers 197 have a length of approximately 3 millimeters. By placing markers along the tubular member, it is possible to ascertain the position of the graft 55 and to determine whether the graft 55 has twisted between its superior and inferior ends 171, 172. Under fluoroscopy, the markers will be exhibited as a relatively straight lines for an untwisted graft, wherein a twisted graft will be revealed by a non-parallel pattern of markers. By placing the markers at equal increments apart, it is possible to use fluoroscopy to ascertain longitudinal compression or tension on the graft.

The sizing of the graft 55 may be performed on a patient-by-patient basis, or a series of sizes may be manufactured to adapt to most patient needs. For the repair of a thoracic aneurysm, the length of the graft 55 is selected so to span approximately one centimeter superior and one centimeter inferior of the aneurysm, wherein the wall engaging members 195 and 196 of the graft can seat within normal tissue of the vessel on both sides of the aneurysm. Thus, the graft should be about two centimeters longer than the aneurysm being repaired. During the pre-implant fluoroscopy procedure, a conventional pigtail angiography catheter is used to determine the locations of proximal arteries to ensure they will not be covered by the implanted graft. Similarly, the diameter of the tubular member 170 is selected by measuring the corporeal lumen which will receive the graft by conventional radiographic techniques and then selecting a tubular member having a diameter one millimeter larger than that measured. For specific applications, one or more pleats 198 may be sewn into the walls of the grafts so as to provide a more suitable emplacement within a lumen having a narrow portion (See FIGS. 29–32). The suture material 190 used for affixing the attachment systems to the graft may be used for providing the graft with pleats.

FIG. 12 depicts the distal end of the delivery catheter 50 assembled for deployment. The graft 55 is disposed within the capsule jacket assembly 53. The superior attachment system 175 is removably retained within the superior capsule 93. Likewise, inferior attachment system 176 is removably retained within the proximal capsule 132. The superior cap 92, nose cone 94 and superior capsule 93 are in the retracted or proximal position adjacent to the conical-shaped knob 100. Similarly, control wire 91 is locked (not shown) via control knob 113 in its retracted or proximal position. During initial deployment, the outer shaft member 131 is in its most distal position in relation to inner catheter assembly 51 and is locked in place by the locking ring on the Touhy Borst adapter 147 (not shown).

During initial deployment, the conical-shaped knob 100 is positioned just proximal to the superior cap 92 and is disposed within the superior capsule 93. Moreover, as depicted in FIG. 12, the releasable ties 205, 207 are wrapped around the graft 55 and are placed into engagement with the release wire 57 to thereby place the inferior and superior attachment systems 176, 175 in a collapsed configuration.

Further, the release wire 57 is configured so that it is disposed within the release wire lumen 64 of the inner shaft 61. The release wire 57 first exits the inner shaft 61 through the inferior release wire notch 102 and then passes through the inferior passageway 211 of the graft 55 and through the loops of the inferior releasable tie 207 (see FIGS. 33 and 34). From there, the release wire 57 passes back through the inferior passageway 211 and inferior release wire notch 102 of the inner shaft 61 and back into the release wire lumen 64. The release wire 57 then passes through the release wire lumen 64 until it reaches the second release wire notch 104 formed in the inner shaft 61. The release wire 57 passes through the second notch 104 and through the superior passageway 209 of the graft 55 and through the loops formed in the superior releasable tie 205. Finally, the release wire 57 reenters the inner shaft 61 by again passing through the superior passageway 209 and the second release wire notch 104 and advances distally within the release wire lumen 64. By so configuring the release wire 57, the attachment systems 175, 176 are locked to the inner shaft 61 both radially and axially.

In another embodiment of the delivery catheter 50, it is contemplated to include a second release wire 217 (see FIG. 35). In this embodiment, each release wire is configured to cooperate with one of the releasable ties 205, 207. For instance, the first release wire 57 may be configured to cooperate with the releasable tie 207 attached to the inferior end 172 of the graft and the second release wire 217 may be configured to cooperate with the releasable tie 205 attached to the superior end 171 of the graft 55. Also, in the two release wire system, the first release wire 57 is configured to pass through the inferior notch 102 and the second release wire 217 is configured to pass through the superior or second notch 104. Further, the two release wires may share the release wire lumen 64 or a second release wire lumen may be formed in the inner shaft 69.

Referring again to FIG. 12, it shows the attachment of the anti-elongation wire 59 to the inner shaft 61. In one presently preferred embodiment, the anti-elongation wire 59 is advanced through the anti-elongation wire lumen 66 until it reaches a longitudinal position along the inner shaft 61 near where the graft 55 is loaded in a delivery catheter 50 assembled for deployment. At this longitudinal position, the anti-elongation wire 59 exits the inner shaft 61 through an anti-elongation wire notch 213 and is affixed to the inner shaft 61 by way of an anti-elongation band 215. Formed into the exterior of the inner shaft 61 and positioned on either side of the band 215 may be low profile bumps (not shown) which facilitate retaining the band 215 in place on the inner shaft 61. The anti-elongation wire 59 is inserted through a gap or hole formed in the band 215 and tied into a knot to thereby prevent proximal movement of the anti-elongation wire relative to the inner shaft 61. The anti-elongation wire 59 is similarly affixed to the inner shaft 61 at its proximal end in that it exits the inner shaft 61, passes through another band flanked by low profile bumps (not shown) and is tied in a knot to prevent distal movement of the anti-elongation wire relative to the inner shaft 61. In another presently preferred embodiment, the anti-elongation wire 59 lies outside the inner shaft 61 but is similarly attached to the inner shaft 61 to prevent elongation thereof.

Further, as shown in FIG. 12, the capsule jacket assembly 53 is positioned such that the distal end of the capsule jacket main jacket 160 overlaps at least a portion of the distal capsule 93. During deployment, capsule jacket locking connector 162 (not shown) secures the main jacket in place. Thus, when any movement or force is applied to the handle assembly 110, the entire apparatus 50 moves as a single unit.

By way of example, the following describes a method of repair of an aortic aneurysm using the method comprising the present invention for intraluminal placement of a graft in an aorta. First, a patient is prepared in a conventional manner by use of a guide wire 56, a dilator and sheath (not shown) to open the iliac artery or abdominal aorta or vessel of the patient. The distal end of the delivery catheter 50 is then inserted into the sheath, which has previously been placed in the vessel. In the preferred embodiment of the present invention, inner shaft lumen 63 is provided for receiving the guide wire 56. However, the following procedure may also be used when the guiding member is constructed as part of the inner catheter assembly 51.

As shown in FIG. 36, the guide wire 56 is introduced by the physician into the femoral artery and advanced to the desired location in the aorta 200 and adjacent to the diseased or damaged portion of the vessel 201. The inner catheter assembly 51, the inferior capsule catheter 52, the capsule jacket assembly 53, the control wire assembly 54 and the releasing system are all configured for deployment of the graft as shown in FIGS. 1 and 12. Thus, the assemblies are advanced by the physician as a single unit over the guide wire. The physician uses the handle assembly 110 and the proximal end of the inner shaft member 70 to guide the distal end of the assemblies over the guide wire.

Next, the locking connector 162 of the capsule jacket assembly 53 is loosened to allow movement of the capsule jacket main jacket 160 (See FIG. 1). It is to be noted that the capsule jacket main jacket 160 may be withdrawn prior or subsequent to advancing the graft 55 and delivery catheter 50 to the repair site. While using one hand to firmly grasp the inferior capsule catheter 52 and hold it stationary, the physician grasps the jacket adapter 164 with the other hand and gently pulls the jacket adapter proximally towards the capsule catheter wye adapter 145, as shown in FIG. 37. The capsule jacket assembly 53 is moved to fully expose graft 55 and the inferior and superior capsule assemblies 90, 130. At this time, the releasing system retains the graft 55 within the inferior and superior capsules assemblies 90, 130. The release wire 57 functions to limit relative movement of the ends of the graft 55 and the capsules by engaging the releasable ties 205, 207 wrapped around the graft 55 (see FIG. 12). The locking connector 162 is then tightened to hold the capsule jacket assembly 53 in place.

The control knob 113 is then rotated to cause relative movement between the superior capsule assembly 90 and the inner catheter assembly 51 to expose the superior attachment system 175 (see FIGS. 1, 12 & 38). Rotating the control knob 113 causes the retaining rack 120 to move the control wire 91 in a distal direction. Since the superior cap 92 and superior capsule 93 are secured to the control wire 91, they move in corresponding relationship with the rotation of the control knob 113. As the superior capsule assembly 90 is moved from engagement with the superior attachment system 175, the conical-shaped knob is exposed, creating a smooth profile at the proximal end of the superior capsule to thereby facilitate removal of the superior end of the delivery catheter from within the implanted graft. At this point, the anti-elongation wire 59 functions to prevent the inner shaft 61 from stretching. As the control knob 113 is turned, the control wire 91 and superior capsule assembly 90 advance within the vasculature of the patient. However, if the inner shaft 61 is easily stretched and if the distal end of the catheter is bent relative to the superior capsule assembly 90, the force advancing the capsule assembly 90 may stretch the inner shaft 61 rather than slide the capsule assembly 90 distally on the inner shaft 61. The anti-elongation wire prevents this.

As shown in FIG. 39, with the handle assembly 110 held firmly in place, the inferior capsule catheter 52 is next moved proximally, which results in the inferior attachment system 176 to be removed from the inferior capsule assembly 130 (see also FIGS. 1 & 12). Once the inferior attachment system 176 is free of the inferior capsule assembly 130, the release wire 57 can be withdrawn from engagement with the superior and inferior ties 205, 207 to thereby allow the attachment systems 175, 176 to spring open and engage the walls of the lumen (see FIGS. 40, 41). The ties 205, 207 remain attached to the exterior of the graft and out of blood flow. The force with which the attachment systems 175, 176 spring open, in conjunction with the forces applied by the blood present in the aorta against the interior of the graft 55, operates to seat the attachment systems of the graft 55 within the aorta.

Although the method of deployment described involved removing each attachment system from the capsules prior to withdrawing the release wire 57, it is to be understood that, for example, the superior attachment system 175 can be removed from the superior capsule assembly 90 and the release wire 57 withdrawn to allow the superior attachment system 175 to engage the walls of the lumen prior to doing the same with the inferior attachment system 176 so that the inferior attachment system 176 engages the lumen. Further, it is important to avoid placing the graft 55 in excessive longitudinal tension, as such a condition may cause the graft 55 to close should it be deployed in a curved position of a lumen. To avoid placing the graft 55 in such a condition, the end of the graft 55 which is yet to be deployed can be moved toward the end of the graft 55 that has been deployed.

When the graft 55 is seated within the aorta, the wall engaging members 195 of the superior attachment system 175 point proximally and with the direction of blood flow, whereas the wall engaging members 195 of the inferior attachment system 176 point distally and against the direction of blood flow. By so orienting the wall engaging members 195, the graft 55 is prevented from migrating downstream or upstream within the aorta. The wall engaging members 195 of the superior attachment system 175 prevent the graft 55 from migrating downstream in response to forces applied to the graft 55 by the direction of blood flow. Similarly, the wall engaging members 195 of the inferior attachment system 176 prevent the graft from migrating upstream in response to forces applied by the blood within the aorta.

A number of the steps of the previously described method for placing the graft 55 within a vessel lumen may be reordered so that the inferior end 172 of the graft 55 may be attached within the lumen prior to attaching the superior end 171 of the graft 55 within the lumen. This alternate procedure may be preferred when repairing a thoracic aortic aneurysm because of the high blood flow and flow rate in the thoracic region of the aorta. By attaching the inferior end of the graft first, the drag on the partially implanted graft may be minimized, thereby avoiding the potential problem of the graft 55 being forced from engagement with the vessel lumen.

In order to attach the inferior end 172 of the graft 55 within the lumen prior to attaching the superior end 171 within the lumen, the two release wire system (see FIG. 35) may be employed. By withdrawing the first release wire 57 prior to withdrawing the second release wire 217, the inferior attachment system 176 can be permitted to engage the walls of the lumen before the superior attachment system 175 does so, to thereby attach the inferior end 172 of the graft 55 within the lumen before the superior end 171 is attached within the lumen. The second release wire 217 can then be withdrawn to attach the superior end 171 of the graft 55 within the lumen. This dual release wire system can also be used to attach the superior end 172 of the graft 55 within the lumen first.

As a final step in any of the methods employed, the delivery catheter is removed from the patient (not shown). The superior capsule assembly 90 and distal end of the inner shaft 61 are moved proximal relative to the graft 55 by first loosening the locking ring 147 (See FIG. 1). Then, while holding the inferior capsule catheter 52 in place by grasping the wye adapter 145 with one hand, the inner catheter assembly 51 is moved proximally by gently pulling the handle assembly 110 with the other hand. The proximal end of the superior capsule 93 may be mated with the inferior capsule for smooth transition.

Finally, the capsule jacket locking connector 162 is loosened. While holding the capsule jacket adapter 164 in place, the inner catheter assembly and inferior capsule catheter 51 and 52 are moved proximally and in unison by gently pulling the wye 145 of the inferior capsule catheter. The catheters are moved until the distal end of the main jacket 163 covers the superior capsule 93 or until the inferior capsule adapter housing 134 mates with the flared transition of the capsule jacket, thereby creating a smooth transition along the entire length of the delivery catheter 50. Thereafter, the inner catheter assembly 57, inferior capsule catheter 52, capsule jacket assembly 53 and control wire assembly 54 are removed from the aorta through the incision. The graft 55 and attachment systems 175 and 176 remain secured to the vessel wall 202, thereby sealing the aneurysm 201 from blood flow.

The entire procedure described herein can be observed under fluoroscopy. The relative positioning of the graft 55 and the delivery catheter 50 can be readily ascertained by the radiopaque attachment systems 175 and 176, radiopaque markers 197 provided on the graft, and the radiopaque marker 87 on the inner shaft 61 (See FIG. 5). If any twisting of the graft has occurred between placement of the superior attachment system and the inferior attachment system, then the twisting can be readily ascertained by observing the series of markers 197. Adjustments to eliminate any twisting which may have occurred can be made before exposing the graft's second extremity 172 by rotation of the catheter 52. Any excessive graft tension or compression can be ascertained by observing the radiopaque markers 197 under fluoroscopy. Adjustments to graft tension can be made before exposing the second extremity of the graft by applying tension on the capsule catheter assembly 52.

Post implant fluoroscopy procedures can be utilized to confirm the proper implantation of the device by the use of a conventional angiographic pigtail catheter or by injecting radiopaque contrast into the guide wire lumen of the balloon catheter shaft. Thereafter the jacket can be removed from the patient and the incisions closed with conventional suturing techniques. Tissues should begin to grow into the graft within two to four weeks. This establishes a complete repair of the aneurysm which had occurred.

While several particular forms of the invention have been illustrated and described, it will be apparent that various modifications can be made without departing from the spirit and scope of the invention. For example, references to materials of construction and specific dimensions are also not intended to be limiting in any manner and other materials and dimensions could be substituted and remain within the spirit and scope of the invention. Accordingly, it is not intended that the invention be limited, except as by the appended claims.

What is claimed is:

1. A system for repairing a lumen, said system comprising:

a graft having a tubular body, a superior end and an inferior end;

a superior attachment system secured to said superior end of said graft and an inferior attachment system secured to said inferior end of said graft, said superior and inferior attachment systems having a first configuration and a second configuration, said first configuration compressed from said second configuration; and a delivery catheter adapted to be placed within the lumen and for placing said graft within the lumen, said delivery catheter having a releasing system, said releasing system including a superior tie to retain said superior attachment system in said first configuration and an inferior tie to retain said inferior attachment system in said first configuration, said superior and inferior ties configured to remain permanent with said graft upon placement of said graft within the lumen and removal of said delivery catheter from the lumen.

2. The system of claim 1, wherein said releasing system further includes at least one release wire cooperating with said superior and inferior ties to retain said superior and inferior attachment systems in said first configuration and to place said superior and inferior attachment systems in said second configuration.

3. The system of claim 2, wherein said delivery catheter includes an anti-elongation wire.

4. The system of claim 3, wherein said delivery catheter includes an inner catheter, an inferior capsule catheter, an inferior capsule assembly attached to said inferior capsule catheter, and a superior capsule assembly, said inner catheter disposed within said inferior capsule assembly, said superior capsule assembly and said inferior capsule catheter;

said inferior capsule catheter, said superior capsule assembly and said inner catheter assembly each adapted to move relative to each other; and said superior capsule assembly adapted to contain said superior attachment system and said inferior capsule assembly adapted to contain said inferior attachment system.

5. The system of claim 4, wherein said delivery catheter further includes a capsule jacket assembly, said capsule jacket assembly adapted to overlay and move relative to said inferior capsule catheter, said superior capsule assembly and said inner catheter.

6. The system of claim 4, wherein said inner catheter includes a control wire lumen adapted to slidably receive a control wire, said control wire having a distal end secured to said superior capsule assembly.

7. The system of claim 4, wherein said superior capsule assembly includes a flexible and tapered nose cone.

8. The system of claim 4, wherein said inner catheter includes an anti-elongation lumen adapted to receive said anti-elongation wire and at least one notch in communication with said anti-elongation lumen, said anti-elongation wire adapted to exit said anti-elongation lumen through said notch and to be affixed to an exterior of said inner catheter.

9. The system of claim 4, wherein said inner catheter includes a release wire lumen adapted to receive said release wire and at least one notch in communication with said release wire lumen, said release wire exiting said release wire lumen through said at least one notch to engage said tie and to reenter said release wire lumen through said notch.

10. The system of claim 9, wherein said inner catheter includes a conical-shaped knob cooperating with said superior capsule assembly for retracting said superior capsule assembly through said graft.

11. The system of claim 4, wherein said inner catheter includes a release wire lumen, said release wire slidably disposed in said release wire lumen, an inferior notch and a superior notch each in communication with said release wire lumen, said release wire exiting said inferior notch, engaging said inferior tie and reentering said inferior notch, said release wire further exiting said superior notch, engaging said superior tie and reentering said superior notch.

12. The system of claim 11, wherein said superior and inferior ties each include a single suture, each said suture secured at a midpoint to said graft, formed into two loops through which said release wire is threaded and affixed at their ends to said graft.

13. The system of claim 12, wherein each said suture is secured to said graft so that each said suture resides exterior said graft.

14. The system of claim 13, wherein said release wire passes through a wall of said graft near said inferior end of said graft to engage said inferior tie and passes through said wall of said graft near said superior end of said graft to engage said superior tie.

15. The system of claim 13, wherein each said suture is passed through a wall of said graft to engage said release wire.

16. A system for repairing a lumen, said system comprising:

a graft having a tubular body, a superior end and an inferior end;

a superior expandable attachment system secured to said superior end of said graft and an inferior expandable attachment system secured to said inferior end of said graft, said superior and inferior expandable attachment systems having a first configuration and a second configuration, said first configuration compressed from said second configuration; and a delivery catheter for placing said graft within the lumen, said delivery catheter having a releasing system, said releasing system including a superior tie to retain said superior expandable attachment system in said first configuration and an inferior tie to retain said inferior expandable attachment system in said first configuration, wherein said delivery catheter includes an inner catheter, an inferior capsule catheter, an inferior capsule assembly attached to said inferior capsule catheter, and a superior capsule assembly, said inner catheter disposed within said inferior capsule assembly, said superior capsule assembly and said inferior capsule catheter;

said inferior capsule catheter, said superior capsule assembly and said inner catheter assembly each adapted to move relative to each other; and said superior capsule assembly adapted to contain said superior expandable attachment system and said inferior capsule assembly adapted to contain said inferior expandable attachment system.

17. The system of claim 16, wherein said releasing system further includes at least one release wire cooperating with said superior and inferior ties to retain said superior and inferior expandable attachment systems in said first configuration and to place said superior and inferior expandable attachment systems in said second configuration.

18. The system of claim 17, wherein said delivery catheter includes an anti-elongation wire.

19. The system of claim 16, wherein said delivery catheter further includes a capsule jacket assembly, said capsule jacket assembly adapted to overlay and move relative to said inferior capsule catheter, said superior capsule assembly and said inner catheter.

20. The system of claim 16, wherein said inner catheter includes a control wire lumen adapted to slidably receive a control wire, said control wire having a distal end secured to said superior capsule assembly.

21. The system of claim 16, wherein said superior capsule assembly includes a flexible and tapered nose cone.

22. The system of claim 16, wherein said inner catheter includes an anti-elongation lumen adapted to receive said anti-elongation wire and at least one notch in communication with said anti-elongation lumen, said anti-elongation wire adapted to exit said anti-elongation lumen through said notch and to be affixed to an exterior of said inner catheter.

23. The system of claim 16, wherein said inner catheter includes a release wire lumen adapted to receive said release wire and at least one notch in communication with said release wire lumen, said release wire exiting said release wire lumen through said at least one notch to engage said tie and to reenter said release wire lumen through said notch.

24. The system of claim 23, wherein said inner catheter includes a conical-shaped knob cooperating with said superior capsule assembly for retracting said superior capsule assembly through said graft.

25. The system of claim 16, wherein said inner catheter includes a release wire lumen, said release wire slidably disposed in said release wire lumen, an inferior notch and a superior notch each in communication with said release wire lumen, said release wire exiting said inferior notch, engaging said inferior tie and reentering said inferior notch, said release wire further exiting said superior notch, engaging said superior tie and reentering said superior notch.

26. The system of claim 25, wherein said superior and inferior ties each include a single suture, each said suture secured at a midpoint to said graft, formed into two loops through which said release wire is threaded and affixed at their ends to said graft.

27. The system of claim 26, wherein each said suture is secured to said graft so that each said suture resides exterior said graft.

28. The system of claim 27, wherein said release wire passes through a wall of said graft near said inferior end of said graft to engage said inferior tie and passes through said wall of said graft near said superior end of said graft to engage said superior tie.

29. The system of claim 27, wherein each said suture is passed through a wall of said graft to engage said release wire.

30. A system for repairing a lumen, said system comprising:
- a graft having a tubular body, a superior end and an inferior end;
- at least one attachment system, said attachment system being secured to one of said ends of said graft, and having a first configuration and a second configuration, said first configuration compressed from said second configuration; and
- a delivery catheter for placing said graft within the lumen, said delivery catheter having a releasing system, said releasing system including a tie to retain said attachment system in said first configuration, said tie configured to remain permanent with said graft upon placement of said graft within the lumen and removal of said delivery catheter from the lumen.

31. The system of claim 30, wherein said releasing system further includes at least one release wire cooperating with said tie to retain said attachment system in said first configuration and to place said attachment system in said second configuration.

32. The system of claim 31, wherein said delivery catheter includes an anti-elongation wire.

33. The system of claim 32, wherein said delivery catheter includes an inner catheter, an inferior capsule catheter, an inferior capsule assembly attached to said inferior capsule catheter, and a superior capsule assembly, said inner catheter disposed within said inferior capsule assembly, said superior capsule assembly and said inferior capsule catheter;
- said inferior capsule catheter, said superior capsule assembly and said inner catheter assembly each adapted to move relative to each other; and
- said superior capsule assembly configured adjacent said superior end of said graft and said inferior capsule assembly configured adjacent said inferior end of said graft.

34. The system of claim 33, wherein said delivery catheter further includes a capsule jacket assembly, said capsule jacket assembly adapted to overlay and move relative to said inferior capsule catheter, said superior capsule assembly and said inner catheter.

35. The system of claim 33, wherein said inner catheter includes a control wire lumen adapted to slidably receive a control wire, said control wire having a distal end secured to said superior capsule assembly.

36. The system of claim 33, wherein said superior capsule assembly includes a flexible and tapered nose cone.

37. The system of claim 33, wherein said inner catheter includes an anti-elongation lumen adapted to receive said anti-elongation wire and at least one notch in communication with said anti-elongation lumen, said anti-elongation wire adapted to exit said anti-elongation lumen through said notch and to be affixed to an exterior of said inner catheter.

38. The system of claim 33, wherein said inner catheter includes a release wire lumen adapted to receive said release wire and at least one notch in communication with said release wire lumen, said release wire exiting said release wire lumen through said at least one notch to engage said tie and to reenter said release wire lumen through said notch.

39. The system of claim 38, wherein said inner catheter includes a conical-shaped, knob cooperating with said superior capsule assembly for retracting said superior capsule assembly through said graft.

40. The system of claim 33, wherein said inner catheter includes a release wire lumen, said release wire slidably disposed in said release wire lumen, and at least one notch in communication with said release wire lumen, said release wire exiting said notch, engaging said tie and reentering said notch.

41. The system of claim 40, wherein said tie includes a single suture, said suture secured at a midpoint to said graft, formed into two loops through which said release wire is threaded and affixed at their ends to said graft.

42. The system of claim 41, wherein said suture is secured to said graft so that said suture resides exterior said graft.

43. The system of claim 42, wherein said release wire passes through a wall of said graft to engage said tie.

44. The system of claim 42, wherein said suture is passed through a wall of said graft to engage said release wire.

* * * * *

UNITED STATES PATENT AND TRADEMARK OFFICE
CERTIFICATE OF CORRECTION

PATENT NO. : 5,693,083
DATED : Dec. 2, 1997
INVENTOR(S) : Steve G. Baker, Michael D. Dake, David C. Dillow It is certified that error appears in the above-identified patent and that said Letters Patent is hereby corrected as shown below: Item [63], Title page, Under "Related U.S. Application Data", Next to last line, Change "Dec. 9, 1993", To read --Dec. 9, 1983--.

Signed and Sealed this

Tenth Day of March, 1998

Attest:

BRUCE LEHMAN

Attesting Officer

Commissioner of Patents and Trademarks